(12) United States Patent
Annest et al.

(10) Patent No.: US 9,211,115 B2
(45) Date of Patent: Dec. 15, 2015

(54) LOCATION, TIME, AND/OR PRESSURE DETERMINING DEVICES, SYSTEMS, AND METHODS FOR DEPLOYMENT OF LESION-EXCLUDING HEART IMPLANTS FOR TREATMENT OF CARDIAC HEART FAILURE AND OTHER DISEASE STATES

(75) Inventors: Lon S. Annest, Tacoma, WA (US); Arthur A. Bertolero, Danville, CA (US); David K. Swanson, Campbell, CA (US)

(73) Assignee: BioVentrix, Inc., San Ramon, CA (US)

( * ) Notice: Subject to any disclaimer, the term of this patent is extended or adjusted under 35 U.S.C. 154(b) by 1965 days.

(21) Appl. No.: 11/751,573

(22) Filed: May 21, 2007

(65) Prior Publication Data

US 2008/0294251 A1    Nov. 27, 2008

(51) Int. Cl.
| | |
|---|---|
| *A61B 17/04* | (2006.01) |
| *A61F 2/24* | (2006.01) |
| *A61B 17/00* | (2006.01) |
| *A61B 17/06* | (2006.01) |

(52) U.S. Cl.
CPC ............ *A61B 17/0401* (2013.01); *A61F 2/2487* (2013.01); *A61B 2017/00243* (2013.01); *A61B 2017/048* (2013.01); *A61B 2017/0496* (2013.01); *A61B 2017/06176* (2013.01)

(58) Field of Classification Search
CPC .............. A61M 1/10; A61F 2/00; A61F 1/00; A61F 13/64; A61B 17/28; A61B 1/00; A61N 1/362
USPC ....................................... 600/25, 37; 606/231
See application file for complete search history.

(56) References Cited

U.S. PATENT DOCUMENTS

| | | |
|---|---|---|
| 4,007,743 A | 2/1977 | Blake |
| 5,295,958 A | 3/1994 | Shturman |
| 5,755,697 A | 5/1998 | Jone et al. |
| 5,810,884 A | 9/1998 | Kim |

(Continued)

FOREIGN PATENT DOCUMENTS

| | | |
|---|---|---|
| EP | 1 078 644 A1 | 2/2001 |
| WO | 00/06028 A1 | 2/2000 |

(Continued)

OTHER PUBLICATIONS

International Search Report and Written Opinion of PCT Application No. PCT/US08/64255, mailed Sep. 29, 2008, 17 pages total.

(Continued)

*Primary Examiner* — Christine H Matthews
(74) *Attorney, Agent, or Firm* — Kilpatrick Townsend & Stockton LLP

(57) ABSTRACT

Devices, systems, and methods for treating a heart of a patient may make use of structures which limit a size of a chamber of the heart, such as by deploying one or more tensile member to bring a wall of the heart and a septum of the heart into contact. A plurality of tension members may help exclude scar tissue and provide a more effective remaining ventricle chamber. The implant may be deployed during beating of the heart, often in a minimally invasive or less-invasive manner. Trauma to the tissues of the heart may be inhibited by selectively approximating tissues while a pressure within the heart is temporarily reduced. Three-dimensional implant locating devices and systems facilitate beneficial heart chamber volumetric shape remodeling.

9 Claims, 17 Drawing Sheets

(56) References Cited

U.S. PATENT DOCUMENTS

| | | | |
|---|---|---|---|
| 5,830,224 A | 11/1998 | Cohn et al. | |
| 5,961,440 A | 10/1999 | Schweich, Jr. et al. | |
| 6,045,497 A | 4/2000 | Schweich et al. | |
| 6,050,936 A | 4/2000 | Schweich, Jr. et al. | |
| 6,059,715 A | 5/2000 | Schweich, Jr. et al. | |
| 6,080,182 A | 6/2000 | Shaw et al. | |
| 6,125,852 A | 10/2000 | Stevens et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,166,684 A | 12/2000 | Yoshikawa et al. | |
| 6,258,021 B1 | 7/2001 | Wilk | |
| 6,260,552 B1 | 7/2001 | Mortier et al. | |
| 6,406,420 B1 | 6/2002 | McCarthy et al. | |
| 6,494,825 B1* | 12/2002 | Talpade | 600/16 |
| 6,511,416 B1 | 1/2003 | Green et al. | |
| 6,572,529 B2 | 6/2003 | Wilk | |
| 6,616,684 B1 | 9/2003 | Vidlund et al. | |
| 6,705,988 B2 | 3/2004 | Spence et al. | |
| 6,709,382 B1 | 3/2004 | Horner | |
| 6,746,471 B2 | 6/2004 | Mortier et al. | |
| 6,776,754 B1 | 8/2004 | Wilk | |
| 6,808,488 B2 | 10/2004 | Mortier | |
| 6,859,662 B2 | 2/2005 | Bombardini | |
| 6,890,295 B2 | 5/2005 | Michels et al. | |
| 7,146,225 B2 | 12/2006 | Guenst et al. | |
| 7,326,177 B2 | 2/2008 | Williamson | |
| 7,390,329 B2 | 6/2008 | Westra et al. | |
| 7,722,523 B2 | 5/2010 | Mortier et al. | |
| 7,753,923 B2 | 7/2010 | St. Goar et al. | |
| 7,766,816 B2 | 8/2010 | Chin et al. | |
| 7,785,248 B2 | 8/2010 | Annest et al. | |
| 8,066,766 B2 | 11/2011 | To et al. | |
| 8,123,668 B2 | 2/2012 | Annest et al. | |
| 8,394,008 B2 | 3/2013 | Annest et al. | |
| 8,425,402 B2 | 4/2013 | Annest et al. | |
| 8,449,442 B2 | 5/2013 | Annest et al. | |
| 8,491,455 B2 | 7/2013 | Annest et al. | |
| 8,506,474 B2 | 8/2013 | Chin et al. | |
| 8,636,639 B2 | 1/2014 | Annest et al. | |
| 2001/0041821 A1 | 11/2001 | Wilk | |
| 2002/0058855 A1 | 5/2002 | Schweich, Jr. et al. | |
| 2002/0077524 A1 | 6/2002 | Schweich, Jr. et al. | |
| 2002/0120298 A1 | 8/2002 | Kramer et al. | |
| 2002/0123768 A1 | 9/2002 | Gilkerson et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2002/0198563 A1 | 12/2002 | Gainor et al. | |
| 2003/0032979 A1* | 2/2003 | Mortier et al. | 606/213 |
| 2003/0163165 A1 | 8/2003 | Bornzin et al. | |
| 2003/0166992 A1 | 9/2003 | Schweich, Jr. et al. | |
| 2003/0181951 A1 | 9/2003 | Cates | |
| 2004/0167544 A1 | 8/2004 | Mann et al. | |
| 2004/0225304 A1 | 11/2004 | Vidlund et al. | |
| 2005/0065506 A1 | 3/2005 | Phan | |
| 2005/0096498 A1 | 5/2005 | Houser et al. | |
| 2005/0137688 A1 | 6/2005 | Salahieh et al. | |
| 2005/0143620 A1* | 6/2005 | Mortier et al. | 600/37 |
| 2005/0192599 A1 | 9/2005 | Demarais | |
| 2005/0288613 A1 | 12/2005 | Heil, Jr. | |
| 2006/0135962 A1 | 6/2006 | Kick et al. | |
| 2006/0161040 A1 | 7/2006 | McCarthy et al. | |
| 2006/0161238 A1 | 7/2006 | Hall | |
| 2006/0200002 A1 | 9/2006 | Guenst | |
| 2006/0241340 A1 | 10/2006 | Schroeder et al. | |
| 2006/0247672 A1 | 11/2006 | Vidlund et al. | |
| 2006/0276684 A1 | 12/2006 | Speziali | |
| 2007/0010876 A1 | 1/2007 | Salahieh et al. | |
| 2007/0049971 A1 | 3/2007 | Chin et al. | |
| 2007/0055303 A1* | 3/2007 | Vidlund et al. | 606/213 |
| 2007/0073274 A1 | 3/2007 | Chin et al. | |
| 2007/0112244 A1* | 5/2007 | McCarthy et al. | 600/16 |
| 2007/0161846 A1* | 7/2007 | Nikolic et al. | 600/16 |
| 2007/0203503 A1 | 8/2007 | Salahieh et al. | |
| 2008/0082132 A1 | 4/2008 | Annest et al. | |
| 2008/0097148 A1 | 4/2008 | Chin et al. | |
| 2008/0269551 A1 | 10/2008 | Annest et al. | |
| 2009/0093670 A1 | 4/2009 | Annest et al. | |
| 2009/0270980 A1 | 10/2009 | Schroeder et al. | |
| 2010/0010538 A1 | 1/2010 | Juravic et al. | |
| 2010/0016655 A1 | 1/2010 | Annest et al. | |
| 2010/0057000 A1 | 3/2010 | Melsheimer et al. | |
| 2010/0268020 A1 | 10/2010 | Chin et al. | |
| 2011/0160750 A1 | 6/2011 | Annest et al. | |
| 2012/0190958 A1 | 7/2012 | Annest et al. | |
| 2013/0090523 A1 | 4/2013 | Van Bladel et al. | |
| 2013/0090672 A1 | 4/2013 | Butler et al. | |
| 2013/0090684 A1 | 4/2013 | Van Bladel et al. | |
| 2013/0096579 A1 | 4/2013 | Annest et al. | |
| 2013/0272100 A1 | 10/2013 | Klinger et al. | |
| 2013/0325041 A1 | 12/2013 | Annest et al. | |
| 2014/0031613 A1 | 1/2014 | Annest et al. | |
| 2014/0051916 A1 | 2/2014 | Chin et al. | |

FOREIGN PATENT DOCUMENTS

| | | |
|---|---|---|
| WO | 02/30335 A2 | 4/2002 |
| WO | 03/032818 A3 | 4/2003 |
| WO | 2005/092203 A1 | 10/2005 |
| WO | 2006/044467 A2 | 4/2006 |
| WO | WO 2007/022519 A2 | 2/2007 |

OTHER PUBLICATIONS

International Search Report and Written Opinion of PCT/US2012/058106, mailed Nov. 26, 2012, 14 pages.
International Search Report and Written Opinion of PCT/US2012/58176, mailed Jan. 8, 2013, 19 pages.
International Search Report and Written Opinion of PCT Application No. PCT/US12/58074, mailed Mar. 13, 2013, 18 pages.
Extended European Examination Report of EP Patent Application 06802038.7 dated Nov. 12, 2013, 13 pages.
International Search Report and Written Opinion of PCT/US2012/058182, mailed Mar. 1, 2013, 19 pages.
International Report on Patentability of PCT/US2012/058074 dated Apr. 10, 2014, 8 pages.
International Report on Patentability of PCT/US2012/058176 dated Apr. 10, 2014, 11 pages.
European Examination Report of EP Patent Application 05810316.9 dated Mar. 10, 2009, 6 pages.
International Search Report and Written Opinion of PCT Application No. PCT/US06/32663, Jul. 31, 2007, 5 pages.
International Search Report and Written Opinion of PCT Application No. PCT/US2005/036690, mailed Jul. 9, 2007, 6 pages.
International Search Report and Written Opinion of PCT Application No. PCT/US09/51288, mailed Sep. 15, 2009, 9 pages.
International Search Report and Written Opinion of PCT Application No. PCT/US06/22594, mailed Oct. 1, 2008, 9 pages.
International Search Report and Written Opinion of PCT Application No. PCT/US08/78810, mailed Feb. 12, 2009, 11 pages.

* cited by examiner

| BSA | 1.76 | M² |
| --- | --- | --- |
| Desired LVEDV/I | 60 | CC/M² |
| Long Axis Location | 6.6 | CM from Annulus |
| Measured EDD at Location | 6.9 | CM |
| Desired EDD at Location | 4.2 | CM |
| Circumference Reduction | 8.0 | CM | ial activities. Various drugs
LOCATION, TIME, AND/OR PRESSURE DETERMINING DEVICES, SYSTEMS, AND METHODS FOR DEPLOYMENT OF LESION-EXCLUDING HEART IMPLANTS FOR TREATMENT OF CARDIAC HEART FAILURE AND OTHER DISEASE STATES

CROSS-REFERENCES TO RELATED APPLICATIONS

The present application is related to that of U.S. patent application Ser. No. 11/536,553, filed on Sep. 28, 2006; and to that of PCT application no. PCT/US06/32663, filed on Aug. 1, 2006; the disclosures of which are incorporated herein by reference.

BACKGROUND OF THE INVENTION

The present invention is generally directed to improved devices, systems, and methods for treatment of the heart. Exemplary embodiments provide implants and methods for alleviating congestive heart failure and other progressive diseases of the heart. Congestive heart failure may, for example, be treated using one or more implants which are selectively positioned relative to a septum and wall of the heart so as to exclude scar tissue and limit a cross section across a ventricle. Trauma to the heart tissues may be inhibited by decreasing a size of the heart chamber and/or approximating tissues when stress on the tissues is limited. Implant locations and overall chamber remodeling achieved by a plurality of implants may be determined so as to provide a beneficial volumetric chamber shape. Exemplary axially curved catheter bodies may enhance measurements for and implant positioning control over such remodeling.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunctions due to rheumatic fever or other causes, cardiomyopathy (a primary disease of the heart muscle itself), congenital heart defects, infections of the heart tissues, and the like. However, in most cases congestive heart failure may be triggered by a heart attack or myocardial infarction. Heart attacks can cause scar tissue that interferes with the heart muscle's healthy function, and that scar tissue can progressively replace more and more of the heart tissue. More specifically, the presence of the scar may lead to a compensatory neuro-hormonal response by the remaining, non-infarcted myocardium.

People with heart failure may have difficulty exerting themselves, often becoming short of breath, tired, and the like. As blood flow out of the heart slows, blood returning to the heart through the vascular system decreases, causing congestion in the tissues. Edema or swelling may occur in the legs and ankles, as well as other parts of the body. Fluid may also collect in the lungs, interfering with breathing (especially when lying down). Congestive heart failure may also decrease the ability of the kidneys to remove sodium and water, and the fluid buildup may be sufficient to cause substantial weight gain. With progression of the disease, this destructive sequence of events can cause the eventual failure of the remaining functional heart muscle.

Treatments for congestive heart failure may involve rest, dietary changes, and modified daily activities. Various drugs may also be used to alleviate detrimental effects of congestive heart failure, such as by expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient trauma. While people with mild or moderate congestive heart failure may benefit from these known techniques to alleviate the symptoms and/or slow the progression of the disease, less traumatic therapies which significantly increase the heart function and extend life of congestive heart failure patients has remained a goal.

It has recently been proposed that an insert or implant be placed in the heart of patients with congestive heart failure so as to reduce ventricular volume. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be constricted or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

An exemplary method and implant for closing off a lower portion of a heart ventricle is shown in FIG. 1, and is more fully described in U.S. Pat. No. 6,776,754, the full disclosure of which is incorporated herein by reference. As illustrated in FIG. 1, a patient's heart 24 has been treated by deployment of an implant across a lower portion of the left ventricle 32 between septum 28 and a left wall or myocardium region 34. The implant generally includes a tensile member which extends between anchors 36 and 38.

A variety of alternative implant structures and methods have also been proposed for treatment of the heart. U.S. Pat. No. 6,059,715 is directed to a heart wall tension reduction apparatus. U.S. Pat. No. 6,162,168 also describes a heart wall tension reduction apparatus, while U.S. Pat. No. 6,125,852 describes minimally-invasive devices and methods for treatment of congestive heart failure, at least some of which involve reshaping an outer wall of the patient's heart so as to reduce the transverse dimension of the left ventricle. U.S. Pat. No. 6,616,684 describes endovascular splinting devices and methods, while U.S. Pat. No. 6,808,488 describes external stress reduction devices and methods that may create a heart wall shape change. Each of these patents is also incorporated herein by reference.

While these and other proposed implants may help surgically remedy the size of the ventricle as a treatment of congestive heart failure and appear to offer benefits for many patients, still further advances would be desirable. In general, it would be desirable to provide improved devices, systems, and methods for treatment of congestive heart failure and other disease conditions of the heart. It would be particularly desirable if such devices and techniques could increase the overall therapeutic benefit for patients in which they are implanted, and/or could increase the number of patients who might benefit from these recently proposed therapies. Ideally, at least some embodiments would include structures and or methods for prophylactic use, potentially altogether avoiding some or all of the deleterious symptoms of congestive heart failure after a patient has a heart attack, but before foreseeable disease progression. It would be advantageous if these improvements could be provided without overly complicating the device implantation procedure or increasing the trauma to the patient undergoing the surgery, ideally while significantly enhancing the benefits provided by the implanted device.

BRIEF SUMMARY OF THE INVENTION

The present invention generally provides improved devices, systems, and methods for treating a heart of a patient. Embodiments of the invention may make use of structures which limit a size of a chamber of the heart, such as by deploying one or more tensile member to bring a wall of the heart and a septum of the heart toward each other (and often into contact). A plurality of tension members may help exclude scar tissue and provide a more effective remaining ventricle chamber. Embodiments of the implant may be deployed at least in part during beating of the heart, often in a minimally invasive or less-invasive manner than traditional open chest, open heart, and/or bypass-based therapies. Trauma to the tissues of the heart may be inhibited by selectively approximating tissues while a pressure within the heart is temporarily reduced, optionally by applying a limited tension force, by selectively reducing a length of the tension member during diastolic pressure reductions, by selectively blocking blood flow into the heart, by pacing a ventricle of the heart at a rate sufficiently fast to inhibit pressure buildup, and/or the like. Three-dimensional implant locating devices and systems facilitate beneficial heart chamber volumetric shape remodeling, and refined deployment/measurement bodies (optionally having axial curvatures substantially corresponding to an adjacent chamber diameter) increase the accuracy and ease with which such remodeling may be effected. A variety of additional devices and methods for their use are also provided, including a pattern for positioning anchors of implants.

In a first aspect, the invention provides a method for treating a heart. The method comprises decreasing, during beating of the heart, a distance between a first location (that borders a chamber of the heart) and a second location (also bordering the chamber of the heart). The distance is selectively decreased while a pressure within the chamber is temporarily reduced so as to permanently and safely reduce a volume of the chamber.

Prior to initiation of the treatment, beating of the heart will typically induce a relatively high systolic pressure and a relative reduced diastolic pressure. The distance between the first location and the second location will often be selectively and permanently decreased while the pressure within the chamber is less than the pre-treatment systolic pressure. Anchors are typically deployed at the first and second locations, with the locations of the heart tissue being approximated by applying tension between the anchors when pressure in the chamber is less than the systolic pressure. The tension can be applied, for example, by incrementally decreasing a length of a tension member extending between the anchors between systolic pressure peaks using a tension force that is sufficient to overcome the diastolic pressure but which does not result in approximation during the systolic pressure. By avoiding shortening of the tension member (and movement of the anchors away from each other) during the systolic pressure peaks, the stresses imposed on the beating heart may be maintained within safe limits. In other embodiments, blood flow into the chamber may be inhibited so as to temporarily decrease pressure within the chamber, allowing the tension to be selectively applied while again limiting stress to the heart tissues. Expansion of a balloon of a balloon catheter may be used to inhibit the blood flow into the heart. Still further heart pressure limiting techniques may be used, including pacing of the ventricle at a relatively rapid rate, with the rate being sufficiently fast to limit total pressure and stress on the tissues. Suitable ventricle pacing rates may be in a range from about 180 to about 240 beats per minute, typically being between about 200 and 210 beats per minute with adjustments beyond this narrower range for patients with significantly weakened hearts, for limiting blood pressure to a desired range, and/or the like.

In many embodiments, a plurality of laterally off-set implants will be used. The separation distances between anchor pairs of each implant may be decreased so as to effectively exclude scar tissue of the heart from the chamber, thereby mitigating congestive heart failure (CHF) of the heart. Some or all of the anchors may be deployed so as to penetrate scar tissue, rather than viable contractile tissue of the heart. Note that some scar tissue may remain exposed within the treated chamber. At least some of the separation distances may be reduced simultaneously, and/or at least some of the separation distances may be reduced sequentially. The treatment may be performed in an open procedure (often by accessing at least the outer pericardium of the heart and optionally without imposing the trauma of opening the heart chamber itself), in a less invasive manner (such as through a subxiphoid incision or the like) or in a minimally invasive manner (such as through the use of catheter based deployment systems and remote imaging, robotically assisted surgery, or the like).

In another aspect, the invention provides a method for treating a diseased heart. The method comprises reducing, in a first cross section, a first size of a chamber of a heart. The size is reduced by approximation of a first anchor location toward a second anchor location. The anchor locations are disposed near edges of a diseased tissue bordering the chamber. For a second cross section, a second reduction in size of the chamber is determined in response to an axial offset between the first cross section and the second cross section, and in response to a magnitude of the first reduction in cross section of the chamber. The determined second reduction in size of the chamber is effected by deploying third and fourth anchors into tissues of the heart bordering the chamber, and by reducing a length of a tension member extending between the third and fourth anchors.

Optionally, the magnitude of the first or second reduction in cross section may be identified using a body which extends between the locations of an anchor pair. The chamber will typically have a diameter associated with each cross section, and the diameter may define a curvature. The body may have an axial curvature that substantially corresponds to the chamber curvature adjacent the anchor pair, so that approximation of the anchors results in a circumferential reduction in size of the chamber that corresponds to the length of the body extending between the anchor locations. This allows calculation of the effective change in diameter that will be generated by various anchor locations, and may facilitate computation of appropriate volumetric changes along an axial length of the heart chamber to produce a beneficial overall remodeling that enhances pumping effectiveness of the heart. Note that not all of the anchor locations may be dictated by the extent of scar tissue in a particular cross section, though at least some may be. To result in a desired longitudinal cross section of the heart, individual axial cross sections may each be determined at least in part in response to a diseased size of the cross section before treatment, an offset between the first cross section and the cross section to be treated, and a magnitude of the first cross section.

In another aspect, the invention provides a method for treating a diseased heart comprising aligning an anchor pattern template with a chamber of the heart. The anchor pattern template identifies a plurality of anchor locations, and anchors are deployed into the heart tissue per the aligned template. Tension is applied between associated anchors so as to approximate tissue adjacent the associated anchors and reduce an effective size of the chamber.

The anchor pattern template may be inserted into the chamber in a small profile configuration, and may be expanded in situ to a large-profile configuration within the chamber, such as by unrolling a flexible anchor pattern template membrane material from about a catheter or the like. Alternative embodiments might be deployed around an outer surface of the heart or chamber. The anchor pattern template will often be aligned with the scar tissue of the heart so that the desired volumetric remodeling effectively excludes the scar tissue from the chamber.

In another aspect, the invention provides a system for treating a heart. The system comprises first and second anchors for coupling to first and second locations bordering a chamber of the heart. A tension member couples the first anchor with the second anchor. The tension member is configured to be selectively shortened from an elongate configuration to a shortened configuration in situ. A pressure component is configured for fluid communication with the chamber and indicates or effects a reduction in blood pressure for selectively shortening the tension member to reduce size of the chamber. The selective shortening can occur while the heart is beating and the pressure component facilitates selective shortening while pressure within the chamber is temporarily reduced.

In another aspect, the invention provides a system for treating a diseased heart. The system is for use with first and second implants, each implant including a pair of anchors coupleable to associated anchor locations bordering a chamber of the heart. Each implant also includes a tension member for coupling the anchors together so as to reduce, in an associated cross section, a size of the chamber of the heart. The system comprises a processor configured for determining, for at least one of the cross sections, an associated reduction in size of the chamber. The reduction in size of the chamber is determined in response to inputs that include an offset between the first cross section and the second cross section, and a magnitude of another reduction in cross section of the chamber. The processor will often output a display of the determined reduction in size of the chamber. Typically, the processor will be configured to determine the reduction in cross section using electronic data processing circuitry running machine readable programming that embodies instructions for calculating the desired reduction in chamber size.

In yet another aspect, the invention provides a system for diagnosing or treating a diseased heart. A chamber of the heart has a diameter defining a curvature between a first location and a second location. The system comprises a body extendable from the first location to the second location. The body has an axis with an axis curvature substantially corresponding to the curvature of the chamber, so that a curving length of the body between the locations approximates a circumference of the wall between the locations.

In exemplary embodiments, the system will include a plurality of anchor pairs and associated tension members for approximating heart tissues. A processor will also be included, with the processor being configured for determining, for a plurality of cross sections of the heart, an associated treatment of the chamber. Each treatment will comprise a reduction in size of the cross section, and may be determined in response to a diseased size of the chamber in the cross section before the treatment, an offset between the cross sections, and/or a magnitude of at least one of the reductions in cross sectional size of the heart chamber. This cross section-by-cross section calculation of the change in size of the heart chamber may be used to provide the chamber with a desired volumetric shape, with the cross sections often being taken transverse to an axis of a ventricular chamber running from the mitral valve to the lower chamber apex. Use of a curving body (the curve substantially corresponds to that of the chamber wall) allows changes in the circumference of the chamber to be effected with enhanced accuracy.

In another aspect, the invention provides a device for treating a diseased heart. The device is used with a plurality of anchors and/or implants. The device comprises an anchor pattern template for aligning with a chamber of the heart. The anchor pattern template comprises indicia identifying a plurality of anchor locations such that when the anchor pattern template is aligned with the chamber, the plurality of anchors are deployed into tissue of the heart per the indicia, and tension is applied between the deployed anchors so as to approximate the tissue, and effective size of the chamber is reduced.

DETAILED DESCRIPTION OF THE INVENTION

The present invention generally provides improved devices, systems, and methods for treatment of a heart. Embodiments of the invention may be particularly beneficial for treatment of congestive heart failure and other disease conditions of the heart. The invention may find uses as a prophylactic treatment, and/or may be included as at least a portion of a therapeutic intervention.

Myocardial infarction and the resultant scar formation is often the index event in the genesis of congestive heart failure. The presence of the scar may, if left untreated, lead to a compensatory neuro-hormonal response by the remaining, non-infarcted myocardium. The systems, methods, and devices described herein may be applied to inhibit, reverse, or avoid this response altogether, often halting a destructive sequence of events which could otherwise cause the eventual failure of the remaining functional heart muscle.

Embodiments of the present invention may build on known techniques for exclusion of the scar and volume reduction of the ventricle. Unlike known techniques that are often accomplished through open surgery, including left ventricular reconstruction, ventricular restoration, the Dor procedure, and the like, the treatments described herein will often (though not necessarily always) be implemented in a minimally invasive manner. Embodiments of the invention can provide advantages similar to those (for example) of surgical reconstruction of the ventricle, resulting in improved function due to improved dynamics, and by normalizing the downward cycle initiated by the original injury and mediated by the neuro-hormonal disease progression response.

Advantageously, the methods, devices, and systems described herein may allow percutaneous left ventricular scar exclusion and ventricle volume reduction to be applied at any appropriate time during the course of the disease. Rather than merely awaiting foreseeable disease progression and attempting to alleviate existing cardiac dysfunction, the techniques described herein may be applied proactively to prevent some or all of the heart failure symptoms, as well as to reverse at least a portion of any existing congestive heart failure effects, to limit or halt the progression of congestive heart failure, and/or to retard or prevent congestive heart failure disease progression in the future. Some embodiments may, for appropriate patients, limit the impact of myocardial infarction scar formation before heart failure every develops.

Figure 1:
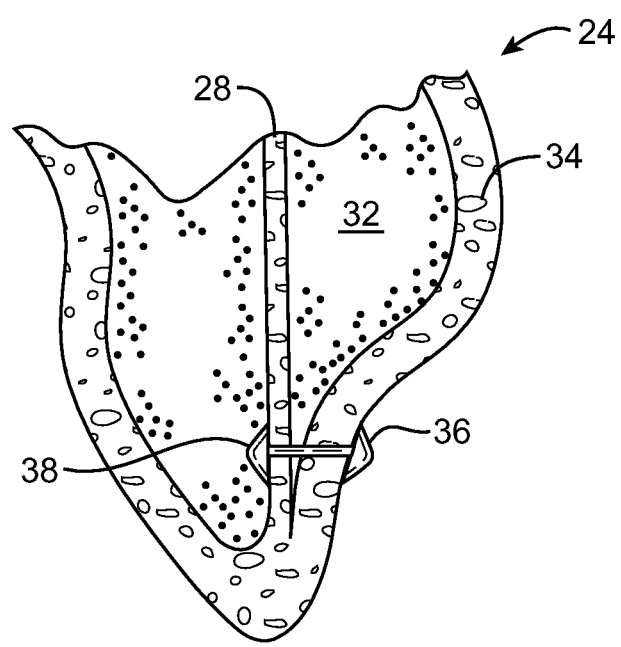
FIG. 1 is a cross-sectional view schematically illustrating a known implant and method for closing off a lower portion of a heart ventricle, as described in the background section.
Figure 2A:
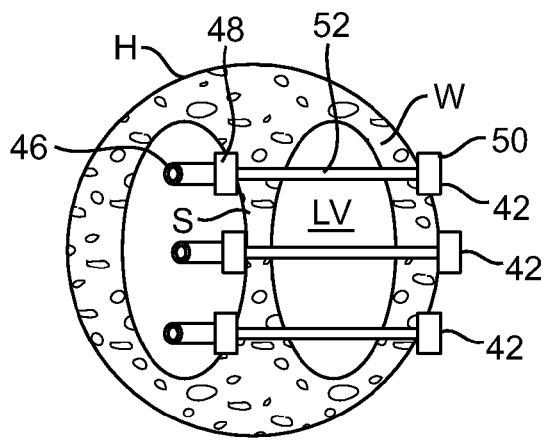
FIGS. 2A and 2B schematically illustrate deployment of three laterally offset implants to effectively exclude a portion of the left ventricle.
Figure 2B:
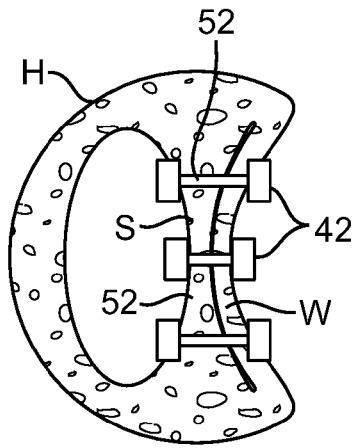
Figure 2C:
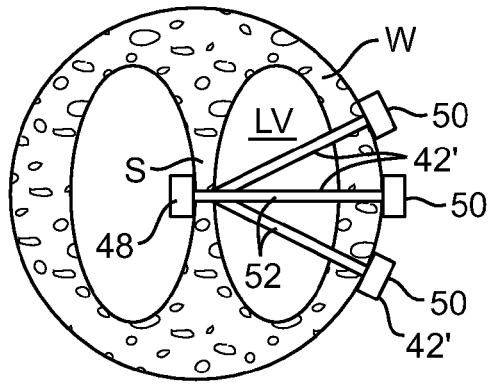
FIGS. 2C and 2D schematically illustrate a single implant having three laterally offset tension members for effectively excluding a region of scar tissue from the left ventricle.
Figure 2D:
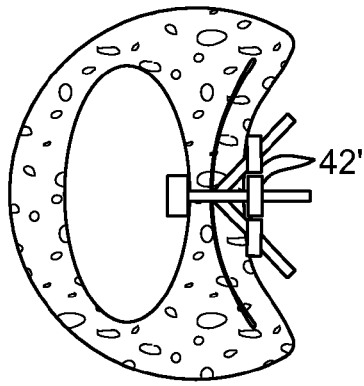
Figure 2:
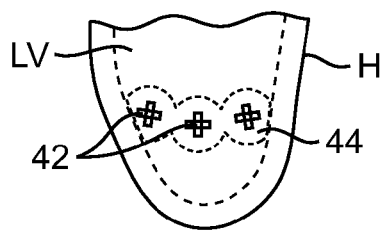
FIG. 2 schematically illustrates a side view of the lower portion of the heart, showing how three implants together reduce the effective size of the left ventricle by effectively excluding a region of scar tissue from the septum and left ventricle wall.

Referring now to the schematic illustration of FIG. 2, a side view of a lower portion of the heart H schematically illustrates how a size of the chamber of the heart can be limited using a plurality of implants. Implants 12 extend through the left ventricle (through the plane of illustration) so that only anchors of the implants are visible on the epicardial surface of the heart. By using a plurality of laterally offset anchors 12, a left ventricle LV is reduced from an initial size to a smaller effective size by engagement between the inner surfaces of the septum and left ventricle wall. A region of engagement 14 between these endocardial surfaces extends between the implants 12 and effectively excludes scar tissue along the lower portion of the septum and/or left ventricular wall from the functioning left ventricle. By arranging the implants 12 across some or all of the left ventricle, the remaining contractile tissue of the ventricle can make effective use of the reduced chamber volume to provide more effective pumping of the blood from within the heart, and may also avoid excessive stagnant voids that remain in fluid communication with the blood flow that might otherwise collect and release thrombus.

Referring now to FIGS. 2A and 2B, a schematic top view shows three laterally offset implants 42 that can be used to, in combination, effectively exclude scar tissue from left ventricle LV. In the illustration of FIG. 2A, each implant is shown in an elongate configuration. More specifically, each implant 42 extends distally from an associated deployment catheter 46 to a distal left ventricular wall anchor 50. A septal anchor 48 is coupled to the wall anchor 50 by a tension member 52. The tension member 52 of the implants 42 are offset laterally, with the tension members here shown extending roughly parallel to each other across the left ventricle LV. In other embodiments, the tension members may be disposed at an angle relative to each other, and may even extend across each other. Nonetheless, by positioning the anchors laterally offset of each other, effective exclusion of scar tissue from the left ventricle LV may be enhanced.

Referring now to FIG. 2B, implants 42 are shown fully deployed, with deployment catheters 46 detached from the implants and removed from the heart, and tension members 52 axially shortened from the elongate configuration of FIG. 2A to a shortened, tensioned configuration. Implants 42 in the shortened configuration draw endocardial surfaces of the wall W into engagement with the corresponding endocardial surfaces of septum S sufficiently to effectively exclude at least a portion of the scar tissue from the functioning lower ventricle. Note that the engagement need not be absolute along the entire cross section of the lower ventricle, so long as scar tissue is effectively excluded immediately after the procedure or, after an initial tissue response to the implant(s), at least some of the scar tissue is not subjected to the stress of being included in the pumping left ventricle. This may improve pumping efficiency of the remaining left ventricle and may limit disease progression from enlarged heart wall tissue stresses.

Referring now to FIGS. 2C and 2D, alternative implants 42' may also include a septal anchor 48 and a wall anchor 50, with a tension member 52 extending therebetween. Such alternative implants may, in some cases, have multiple wall anchors 50 associated with each septal anchor 48, or multiple septal anchors associated with each wall anchor. The tension members 52 may extend in positions that are both angularly and laterally offset from each other. As shown in FIG. 2D, axial shortening of the tension members between the anchors 48, 50 may leave a portion of the tension member extending into the extra-cardiac space. In some embodiments, one or a plurality of implants may provide a bunching engagement of endocardial tissues, with the engagement extending upon multiple fold lines so as to effectively exclude at least a portion of the scar tissue. Some or all of the components of the implants may be positioned using an epicardial access approach, with or without endocardial delivery or deployment catheters 46 (see FIG. 2A) for other implant components.

Figure 3A:
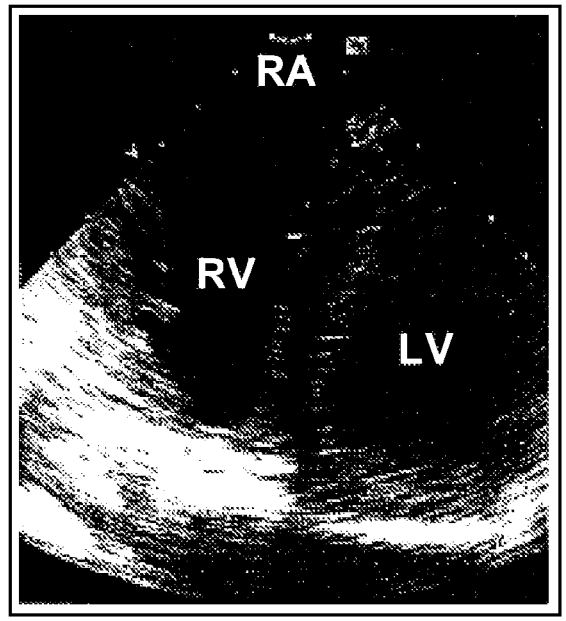
FIGS. 3A and 3B illustrate examples of images of the heart and/or devices disposed therein that may be used to direct deployment of embodiments of the invention.
Figure 3B:
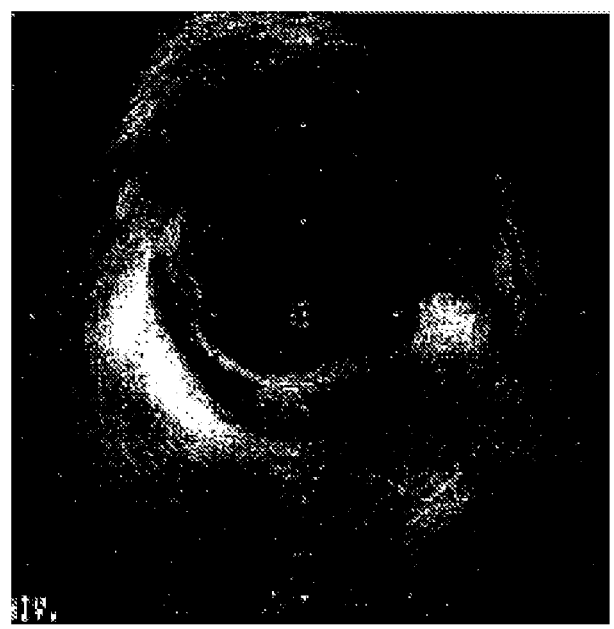

Referring now to FIGS. 3A and 3B, deployment of the implants described herein and implementation of the therapies will benefit from accurate and reliable identification of the margins separating the scar and viable, contractile myocardium. Such identification can be accomplished, for example, using pre-operative imaging, catheter-sensed activation potentials, pacing thresholds, ultrasonic imaging characteristics, biomarkers, or a variety of other tissue imaging and/or characterization methodologies. Additional exemplary tissue characterization (and/or differentiation between scar and viable contractile tissues) may employ MRI tissue characterization techniques with or without the use of contrast agents. In general, it will be beneficial to provide information to the physician deploying the system to allow accurate characterization of selected locations as substantially comprising scar tissue or substantially comprising a viable contractile tissue. Additionally, the geometry of the chambers of the heart, and particularly the left ventricular chamber, should be clearly imaged to facilitate the desired reduction in size of the left ventricular chamber. This imaging may be accomplished by one imaging modality or by a combination of different imaging modalities. Exemplary imaging modalities which may be employed for identification of the heart geometry and/or tissue characterization include: echocardiography (including intracardiac echocardiography ("ICE") and/or extra-cardiac echocardiography (such as transesophageal echocardiography and/or transthoracic echocardiography ("TTE" and "TEE", respectively) or the like), intra- or extra-vascular endoscopy, fluoroscopy, or any of a variety of alternative existing or new imaging techniques, either alone or in combination.

FIGS. 3A and 3B illustrate an example of ICE showing the geometry of the heart chambers, including a right atrium RA, a portion of the right ventricle RV, and the left ventricle LV along with some of the heart tissues bordering these chambers. FIG. 3B illustrates an intracardiac echocardiography image in which a catheter device within the ventricle can be seen.

Deployment of the structures described herein may also benefit from sensors that can be used to monitor the procedure, such sensors ideally providing a real-time assessment of the progress of the treatment and performance of the heart during deployment and/or as deployment is completed. The goal of deployment will often be to achieve a desired reduction in size of a chamber (typically the left ventricle), while avoiding overcorrection (which might otherwise induce acute diastolic dysfunction). Such functional assessment sensors may comprise pressure sensors, hemodynamic sensing systems, strain sensors, oxygen saturation sensors, biological marker detectors, and/or other sensors measuring heart function to permit a quantitative assessment of efficacy of the procedure as it is implemented.

Figures 4A, 4C, 4D:
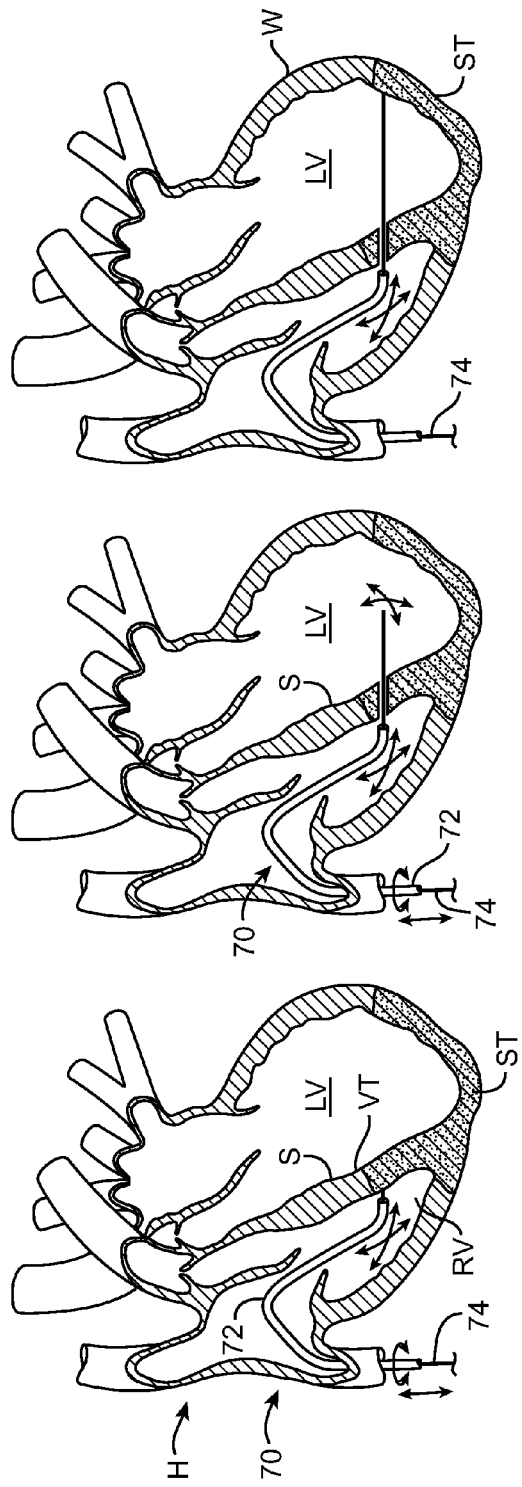
FIGS. 4A-4E are cross-sectional views schematically illustrating methods for accessing, identifying, and penetrating tissues for deployment of the implant system of FIGS. 2 and 2A.
Figures 4B, 4E:
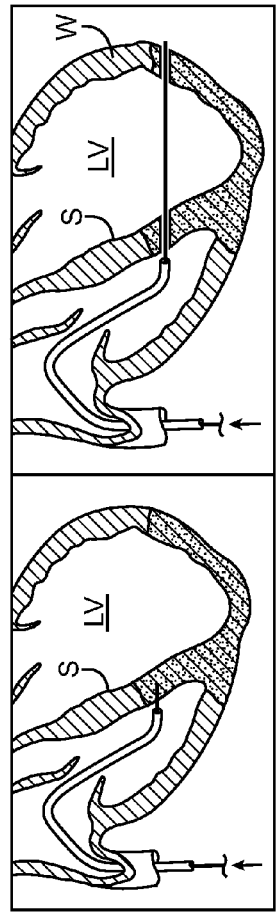

Referring now to FIGS. 4A-4E, exemplary techniques and structures for accessing and penetrating the septum and left ventricular wall can be understood. First summarizing these steps, it will be advantageous to identify, engage, and temporarily hold the device in alignment with a desired position on the right ventricular septum, as schematically illustrated in FIG. 4A. Identification or characterization of the engaged tissue will also be advantageous. The septum will be penetrated as can be understood with reference to FIG. 4B, and the system is steered across the left ventricular chamber as illustrated in FIG. 4C. The system engages one or more target locations on the left ventricular wall as shown in FIG. 4D. The engaged tissue may be characterized and the system repositioned as needed, with the system being held in engagement with the left ventricular wall if found to be at an appropriate or designated position, with the system optionally attaching or temporarily affixing itself to the left ventricular wall. The left ventricular wall may then be perforated, penetrated, or otherwise transcended as illustrated in FIG. 4E. As indicated above regarding FIGS. 3A and 3B, target tissue access, penetration, and implant deployment may be performed with reference to ICE within the blood stream of the vascular system, with the ICE images typically comprising 2-D sector images, the sectors often comprising an about 60 degree sector.

In more detail, referring now to FIG. 4A, an access and deployment system 70 includes a catheter 72 and a penetrating/sensing perforation device 74. In some embodiments, separate probes may be used for penetrating the heart tissues and characterizing the tissues. Here, catheter 72 accesses the right ventricle RV in a conventional manner, typically by advancing the catheter over a coronary access guidewire. A distal end of catheter 72 is aligned with a candidate location along the right ventricular surface of the septum S by a combination of axial rotation of the catheter and distal/proximal positioning of the catheter, as shown by the arrows. Positioning of the catheter is directed with reference to imaging (as described above) and when the end of the catheter is aligned with the candidate location a perforation device 74 is advanced distally so that a distal end of the perforation device contacts the septum S.

Perforation device 74 may characterize or verify that the candidate location is appropriate, for example, by determining a pacing threshold at the candidate site. Scar tissue ST may have a pacing threshold which differs sufficiently from a viable tissue VT to allow the physician to verify that the candidate site comprises scar tissue and/or is otherwise suitable. If the candidate site is not suitable, the perforation device 74 may be withdrawn proximally to disengage the perforation device from the septum S, and the catheter may be repositioned as described above to a new candidate site.

Catheter 72 may comprise a commercially available steerable sheath or introducer. Deflection of catheter 72 may be effected using one or more pull wires extending axially within the catheter body. Suitable introducers include devices that can be introduced transcutaneously into a vein or artery. Suitable steerable sheaths may generally comprise a tubular catheter body with an open working lumen. The open lumen can be used as a conduit for passing another catheter into the patient body, or for introducing another device (such as a pacing lead) into the patient body. Exemplary steerable sheaths for use in system 70 may include those commercially available from the Diag division of the St. Jude Corporation, from Medtronic, from Bard, and/or from others. Preferably, the working lumen of catheter 72 will be in a range from about 5 F-11 F. Alternative systems may employ a flexible sheath removably receiving a steerable catheter or other device therein, the steerable catheter optionally comprising a steerable electrophysiology catheter or a device derived therefrom. Still further embodiments may employ pre-bent cardiac access catheters.

Regarding perforating device 74, one embodiment would comprise a deflectable or steerable catheter body (ideally comprising a 2 F-3 F catheter) with a metallic rounded and/or bullet-shaped electrode at its distal end. The distal electrode is connected to a signal wire that terminates in a connector outside the body. Electrogram amplitudes recorded from the distal electrode can be used to help determine if the distal tip is located over scar tissue or over viable tissue. Efficacy in characterization of engaged heart tissues (between scar tissue and viable heart tissue) may be enhanced by recording the differential signal between the tip electrode and a band electrode located less than 1 cm from the distal electrode.

Pacing from the distal tip can be employed to help avoid perforation through viable myocardium. For most patients, such a perforation site would be counter-indicated. If the heart can be paced from the tip using a 10V amplitude pacing pulse, then viable myocardium will generally be disposed within about 5 mm of the tip. When the proper penetration site has been identified, then the distal tip is electrically coupled to an electrosurgical power source unit, and penetration is enabled by applying power to the tip in cut mode. At proper power settings, this perforation method can allow a clean perforation channel to be created without the tearing that can otherwise occur with physical perforation of the septum or free wall.

Once an appropriate site has been identified and verified, the system is held in alignment with the candidate site, and may optionally be affixed temporarily at the verified site. Perforation device 74 is advanced distally into and through septum S as illustrated in FIGS. 4B and 4C. Perforation device 74 may have a sharpened distal tip, a rotatable helical or screw structure, or other mechanical attributes to facilitate penetration into and perforation through the myocardium. Energy delivery elements (such as electrosurgical energy, laser energy, or the like) may also be provided. In some embodiments, system 70 may employ components similar to or modified from known septum traversing systems used for accessing the left ventricle. In general, it may be advantageous to seek to perforate tissue with an axis of perforation device 74 oriented across the ventricle and straight toward or near a suitable target site for the subsequent perforation, as imposing excessively acute angles on the heart tissue may weaken or even tear the heart tissue.

As can be understood with reference to FIGS. 4C and 4D, once perforation device 74 has penetrated through the septum S, manipulation of the catheter 72 under the guidance of the imaging system allows the perforation device to be steered across the left ventricle LV and into engagement with a target location along the wall of the left ventricle. The tissue at this target location may be characterized using a sensor of perforation device 74, pacing of the engaged tissue, or the like, and the end of the perforation device repositioned as needed. The preferred location for deployment of the implant may be along or adjacent to scar tissue ST. In some embodiments, system 70 may be used for positioning of a lead at a location separated from the axis of the implant tensioning member. System 70 also allows for epicardial lead placement by advancing the perforation device 74 endocardially through septum S and the myocardium of the left ventricular wall W until it is located on the epicardial surface of the heart. The perforation device 74 and/or lead may be at least temporarily fixed at that location and tested for proper pacing effect, as can be understood with reference to FIGS. 4E and 5B.

The access and deployment system 70 described above with reference to FIGS. 4A-4E may be supplemented with or replaced by a number of differing system components. For example, as can be understood with reference to FIG. 5A, a balloon catheter 80 or other sealing structure may be used, optionally being advanced within catheter 72 and/or over perforation device 74. The balloon of balloon catheter 80 may be positioned within the myocardium of septum S or the left ventricular free-wall W to anchor the deployment system temporarily to the heart tissue and control blood loss, particularly blood loss through the left ventricular wall into the extra-cardiac space. In some embodiments, two separate balloons may be used to seal both the septum and the left ventricular wall. Balloons may also be used with or as anchors of the implant device.

Still further alternative structures may be employed, perforation device 74 may have any of a variety of sensors, including pressure sensors and the like. System 70 will often comprise high contrast structures to enhance imaging, such as by including materials having high radio-opacity, echo-density, or the like. As noted above, perforation device 74 may have or be used with a cutting, drilling, or other mechanism to help in tissue penetration. Still further alternative structures may be used for steering and positioning of the deployment system and perforation device. For example, rather than manually manipulating or steering catheter 72 to position and orient the implant, the deployment system may employ robotic surgical techniques such as those now being developed and/or commercialized for manipulation of catheters. Magnetic steering of the catheter end may also be employed, and any of a wide variety of mechanical steerable or preformed catheter structures could be employed. Some or all of the components may access the left and/or right ventricular chambers using an epicardial approach, rather than the endovascular approach described above. A combination of an extra-cardiac and intracardiac approach may also be employed, with the components of the implant being introduced in any of a wide variety of techniques. In some embodiments, implant 42 and/or other components of the system may be deployed in an open surgical procedure. Directly accessing at least the epicardial surface of the heart may significantly facilitate positioning and deployment of implant 42, particularly for development of implant system components and techniques, including those which may later be deployed in a minimally invasive manner.

Figure 5B:
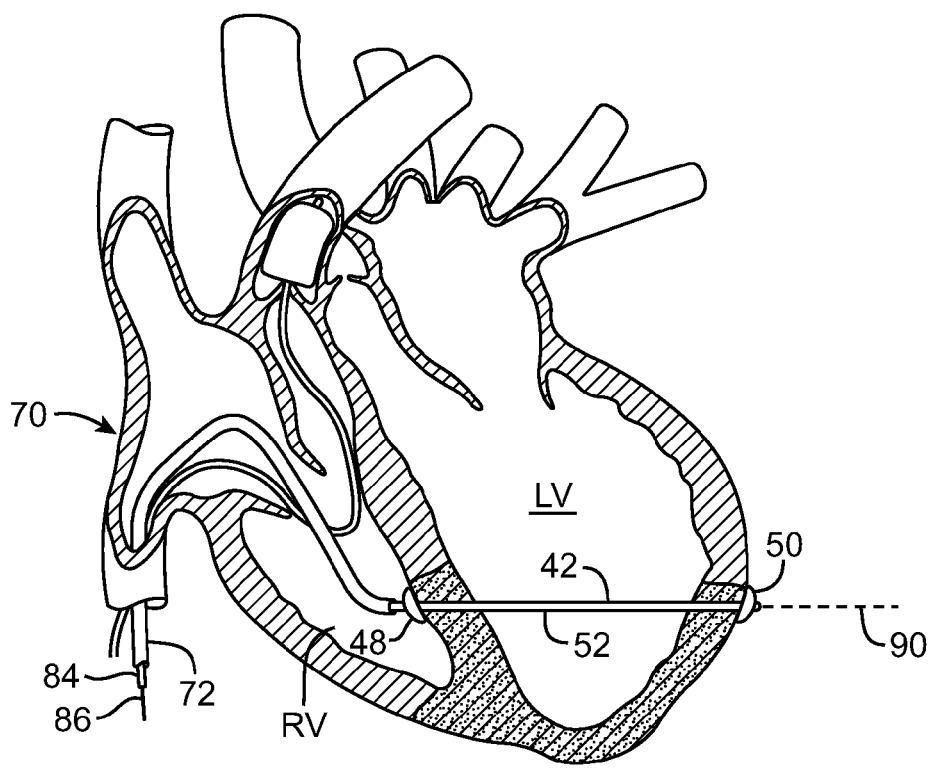
FIGS. 5A and 5B are cross-sectional views schematically illustrating initial deployment of an implant of the system of FIGS. 2A and 2B, with the implant initially being deployed in an elongate configuration.
Figure 6A:
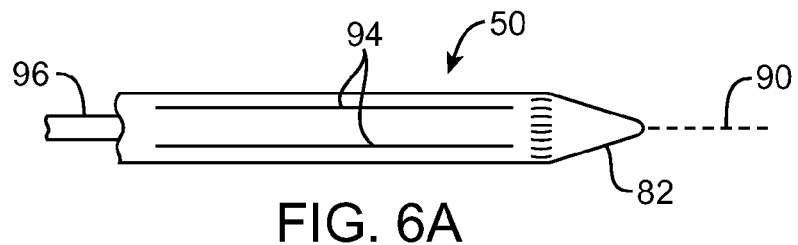
FIGS. 6A-6D illustrate deployment of an anchor for use in the implant of FIG. 5B.
Figure 6B:
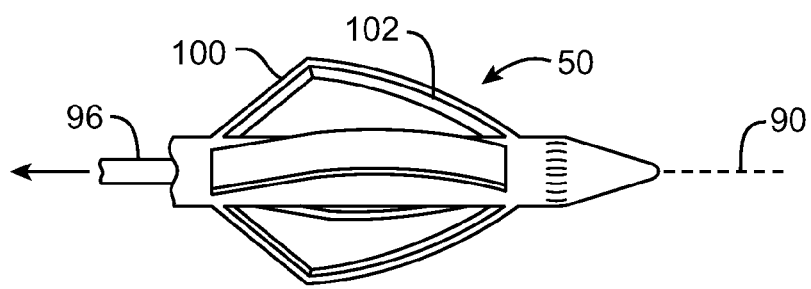
Figure 6C:
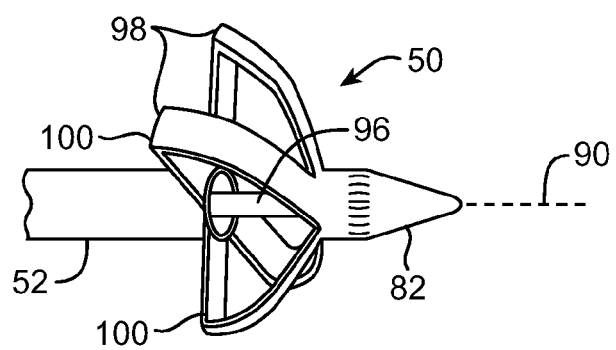
Figure 6D:
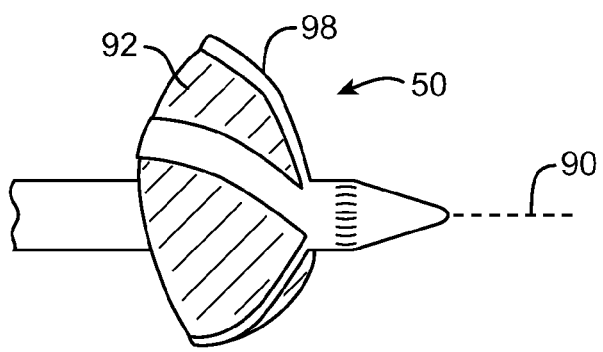

Referring now to FIGS. 5B and 6A-6C, implant 42 is deployed through catheter 72 of deployment system 70, with the implant initially being deployed in an elongate configuration extending across left ventricle LV. Anchors 48, 50 of implant 42 advance distally through a lumen of catheter 72 while the anchor is in a small profile configuration, as illustrated in FIG. 6A. Anchor 50 expands from the small profile configuration to a large profile configuration, which may be effected by altering a distance between a distal end 82 and a shaft of tension member 52 using elongate bodies 84, 86 detachably coupled to the distal end 82 and tension member 52, respectively.

In general, anchors 48, 50 will be deployable through, over, or adjacent to the myocardium tissue penetrating components of deployment system 70. The anchors will attach to or otherwise engage the wall, usually by expanding or inflating into a cross section larger than that of the penetration through the heart tissue. A wide variety of anchor structures may be employed, including structures that form a disk-shaped surface or lateral extensions from an axis 90 of implant 42. As can be understood with reference to FIG. 60, an inflatable bladder 92 or balloon of appropriate shape may be used alone or in combination with other anchoring structures. If an inflatable bladder or balloon is used, it may be filled with a substance which is initially introduced as a liquid, but which reversibly or irreversibly solidifies. Suitable fill materials may, for example, comprise liquid silicone rubber, which can polymerize at any of a variety of alternative desired rates depending on the chemistry of the material used. Optionally, the material may solidify over more than one hour, optionally over many hours or even days at body temperatures. During a procedure, such an injected liquid could be removed if desired, but the material would eventually solidify. Biological adhesives could also be delivered as fluid to fill a balloon, though cure times are relatively shorter for such materials. Such materials would irreversibly solidify.

The septal and left ventricular wall anchors 48, 50 may be identical or similar in structure, or may differ to reflect the differences between the epicardial and endocardial surfaces they engage. Fixation to the wall and septum will generally be sufficient to support the tension of tensile member 52, which will generally be capable of approximating the wall and septum, typically maintaining proximity or engagement between these structures during beating of the heart. Anchors 48, 50 and tensile member 52 will often comprise high-contrast materials to facilitate imaging, such as by including materials of sufficient radio-opacity, echo density, and the like.

In some embodiments, implant 42 may be used alone or with similar implants to effect volume reduction over a length, width, or volume of the ventricular wall. When at least a portion of the implant 42 is deployed using an epicardial approach, left ventricular anchor 50 will often be included in the components attached from outside the heart, with tensile member 52 and/or anchor 48 being attached to this epicardial component during deployment. Robotic structures may be used to position the intracardiac or extra-cardiac components, and/or to attach the two of them together.

Referring again to FIGS. 6A-6D, the exemplary anchor structure comprises a Nitinol™ shaped memory alloy or other flexible material formed into a tubular shaft. Axial cuts 94 may be formed along this tubular shaft, with the cuts having a desired length and being disposed near distal end 82. Anchor 50 is advanced until the most proximal margin of cuts 94 extends clear of the heart tissue. A retraction member 96 (optionally being releasable attached to the associated elongate body 86) fixed to the inside of distal end 82 is retracted proximally, expanding the walls of the tubular shaft radially into the circumferential series of arms 98. Tissue engaging surfaces 100 of arms 98 may be substantially perpendicular to axis 90 of the implant. Arms 98 may have two general components, including the portion of the arm along tissue engaging surface 100 and a slightly longer bracing portion of the arm 102 extending away from the tissue engaging surface along axis 90. The proportionate sizes of these two elements of arms 98 may be pre-determined by localized altering of the arm stiffness (effecting the placement of living hinges) or the tubing material will otherwise preferably bend so that the arms assume a desired shape. The deployed arms may have, for example, the pyramid shape shown with the tissue engaging surface 100 supported by angled portions 102 with a pyramid-like force distribution, the angled bracing portions forming a triangular relationship with the surface of the heart wall.

Member 96 may remain within the deployed anchor, axially affixing tensile member 52 relative to the end of the anchor after deployment of the implant. This can help inhibit collapse of the arms 98. In some embodiments, arms 98 may be biased to the large cross section deployed configuration, such as by appropriate treatments to a shape memory alloy or the like. In such embodiments, member 98 or some other actuation structure may restrain the anchor in a small cross section configuration, it may not remain within the deployed implant after it is expanded.

As can be understood with reference to FIG. 60, once the anchor 50 is deployed and in position, additional support elements may be positioned or deployed through the deployment system 70. For example, a space occupying or expandable structure such as bladder 92 may be positioned or inflated within arms 98, internal support structures (optionally comprising internal pyramid-like support arms) may be deployed. The septal anchor 48 will optionally have a structure similar to anchor 50, with the proximal and distal orientations of the arm structures reversed.

While anchor 50 of FIGS. 6A-6D is shown as being integrated into a tubular shaft of elongate tensile member 52, the anchor or fixation device may alternatively comprise a separate element introduced separately over a guidewire or the like. Still further alternatives may be employed, including fixation of the heart walls by placement of magnetic materials on or within the walls, with the bodies acting as anchors and the magnetic material acting as a tensile component so as to hold the walls in apposition.

Anchors 48 and/or 50 may optionally be drug eluting. For example, bladder or balloon 92 may have a porous surface capable of eluting a substance from the film material. Alternatively, an outer surface of the balloon or the anchor structure itself may comprise a permanent or biodegradable polymer or the like, such as those that have been developed for drug eluting stents and available from a number of commercial suppliers. Drugs eluted from the implants may include any of the compositions eluted from drug-eluting stents.

Figure 5A:
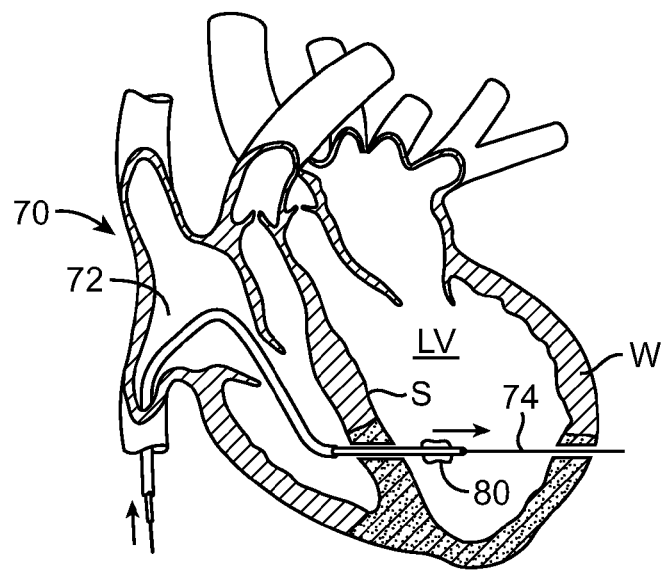
Figure 7B:
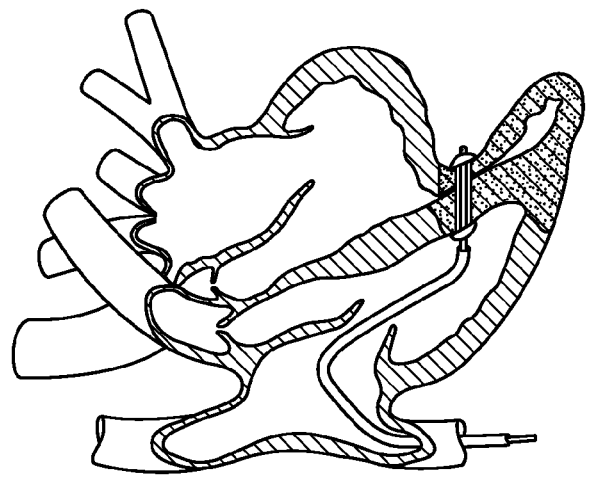
FIGS. 7A and 7B are cross-sectional views schematically illustrating shortening of the tensile member of FIG. 5B from the elongate initial configuration to a shortened deployed configuration so as to reduce a size of the left ventricle and effectively exclude at least a portion of a scar tissue from the left ventricle.
Figure 7A:
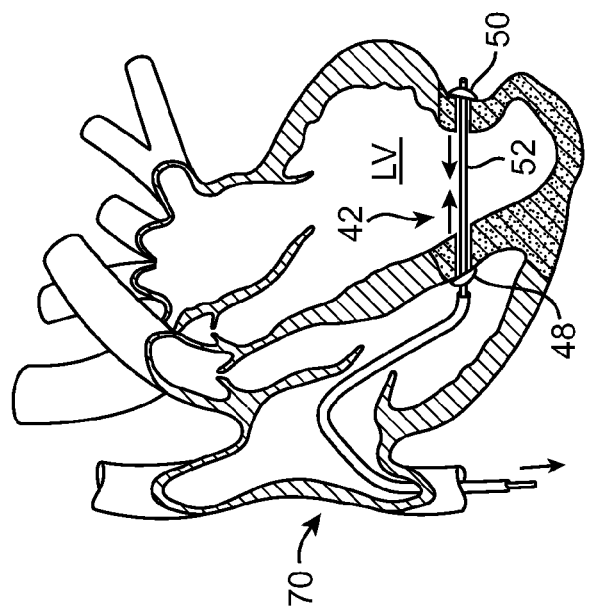

Referring now to FIGS. 5B, 7A, and 7B, after anchors 48-50 are deployed, implant 42 may be shortened from its elongate configuration with a relatively large distance between the anchors along tensile member 52 to a shortened configuration. In some embodiments, the tensile member may comprise a shaft of the tissue penetrating perforation device 74 (see FIGS. 4A-4E). In other embodiments, tensile member 52 will comprise a separate structure. In many embodiments, the tensile member and anchors will remain permanently in the heart to hold the septum and left ventricular wall in apposition. To allow shortening of the tensile member, excess length of the tensile member may be removed with the catheter 72 and other components of the delivery system, and/or some portion of the length of the tensile member may remain in the extra-cardiac space outside the left ventricular wall.

Optionally, a ratchet mechanism may couple the septal anchor 48 to the tensile member 52, with the ratchet mechanism allowing the separation distance between the anchors to gradually decrease. While exemplary ratchet mechanisms are described below with reference to FIGS. 11A-11C, 12A and B, and 14A-14C, a wide variety of alternative structures that can be reconfigured in situ to alter the separation distance between the anchors might alternatively be employed.

Figure 8:
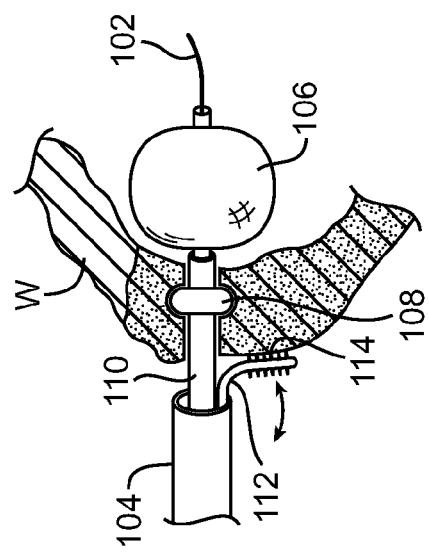
FIG. 8 schematically illustrates an alternative anchor structure in the form of a inflated balloon, an annular balloon disposed within a wall of the left ventricle so as to inhibit blood flow through a perforation, and treating a myocardial tissue surface with mechanical energy from a bur or the like to promote adhesion formation.

Referring now to FIG. 8, additional optional elements for the implants and/or deployment systems described herein can be understood. Here, a guidewire 102 is shown extending through a perforation of left ventricular wall W, with components of the deployment system and/or implant advanced over the guidewire. A deployment catheter sheath 104 may be used with or without guidewire 102. Guidewire 102 and/or sheath 104 may be steerable to facilitate access and deployment of the implant.

A temporary or permanent anchor is here provided by a balloon 106. An axially-oriented portion of the outer surface of balloon 106 engages the adjacent epicardial surface of wall W to pull the wall towards engagement with the septum, as described above. Balloon anchor 106 may comprise a structure similar to a balloon of a balloon catheter, with an expandable and biocompatible bladder material defining the balloon wall. Along with the exemplary fill materials described above, the fill material may generally comprise a reversibly or irreversibly hardenable polymer, and the bladder material may have pores to allow eluting of drugs from the fill material or fluid.

An annular expandable structure such as annular balloon 108 on an associated catheter 110 may expand within the myocardium from the perforation or penetration through the left ventricular wall W or septum S. Balloon 108 may help to temporarily hold the deployment system in position relative to the perforation and tissue structures, or may in some embodiments be used as a permanent anchor (with or without additional anchoring structures). Temporary deployment of balloon 108 against the myocardial tissues may be particularly advantageous during or after perforation of the free left ventricular wall W during deployment of the wall anchor, as it may help to limit the release of blood into the extra-cardiac space. Balloon 108 may comprise a relatively standard balloon catheter material, such as nylon, PET, or the like.

Yet another aspect schematically illustrated in FIG. 8 is a probe 112 having a surface 114 that treats the endocardial surface of the left ventricle wall W or septum S so as to promote formation of adhesions. Surface 114 may comprise a bur or other mechanical energy application surface for imposing mechanical trauma on the tissues within the heart. In alternative embodiments, surface 114 may comprise an electrode surface for applying electrosurgical energy, light refracting surface for applying visible or invisible radiation, one or more agent delivery ports for transmitting caustic or sclerosing agents to the heart tissue, or the like. Such surfaces may apply a controlled, limited trauma to the tissue surface regions of the left ventricular wall and/or septum so as to induce the formation of scar tissues bridging these two tissue structures and forming permanent adhesions therebetween.

When a probe 112 or surface of the implant or delivery catheter is used to promote formations of adhesions, or when the implant provides sufficient compressive force between the left ventricular wall and septum so as to promote adhesions without separately imposing a trauma on the tissue surface, some or all of the implant may comprise biodegradable material. After the adhesions are fully formed and the biodegradable material of the implant degrades, the natural adhesions may alone maintain the reduced size of the left ventricle, exclude scar tissue from the effective left ventricle, and limit the effects of congestive heart failure. Suitable biodegradable materials for use in the structural components of the implants described herein may include materials developed for and/or used in biodegradable stent structures.

While an myocardial engagement balloon 108, balloon anchor 106, and trauma inducing probe 112, are shown schematically together in FIG. 8, and while some embodiments of the methods and systems described herein may make use of all three of these components, many embodiments may employ only any one or any two of these optional structures. Additionally, while much of the above-description relates to intravascular access and deployment of at least a portion of the implant, other embodiments may be deployed during laparoscopic or even open heart surgery. Such embodiments may be particularly beneficial for verification and tailoring of the pattern of multiple implants to be used for scar tissue exclusion and left ventricular volume reduction, with subsequent embodiments making use of the verified and/or refined patterns through an at least partially intravascular approach.

Figure 9:
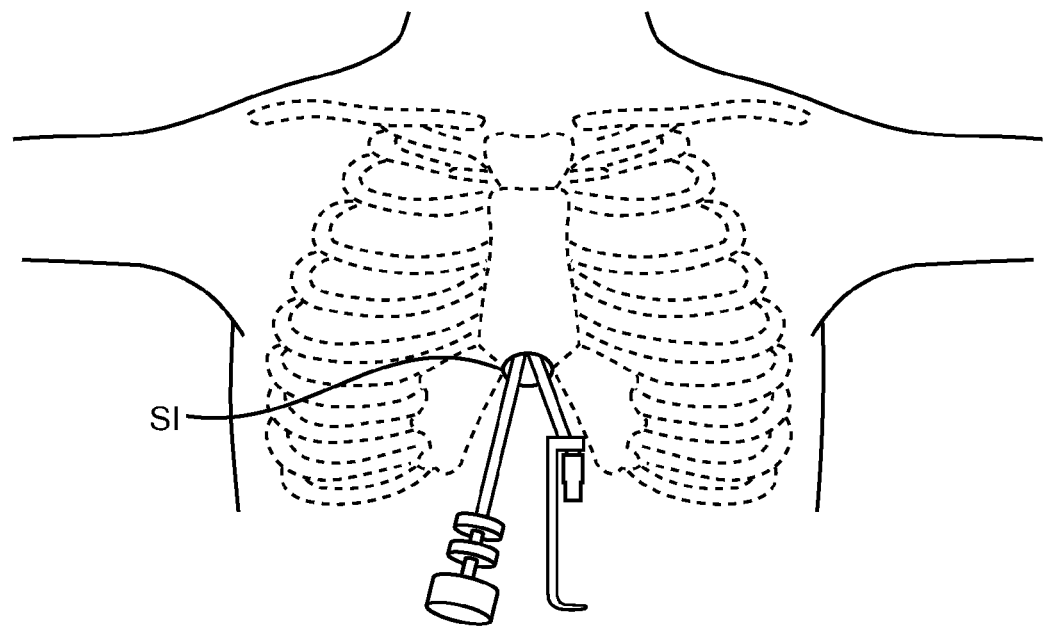
FIG. 9 schematically illustrates accessing the heart via a subxiphoid incision.
Figure 10:
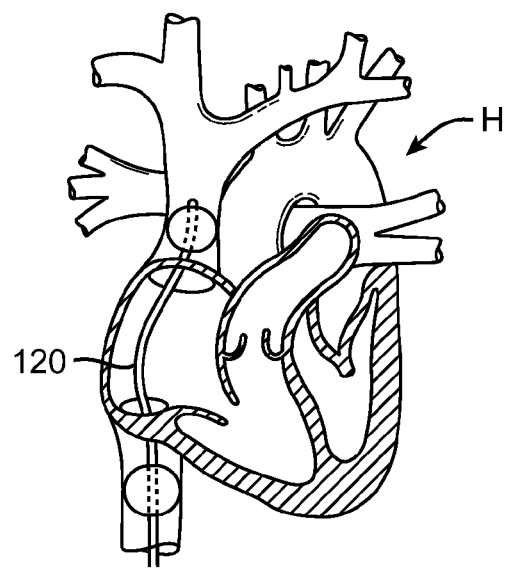
FIG. 10 illustrates a method for unloading of the heart with a double balloon catheter.

Referring now to FIG. 9, embodiments of the invention may be deployed using a subxiphoid incision SI to access the heart, and/or the ventricles of the heart. In some embodiments, additional access may be obtained through one or more intercostals space for one or more instruments. As shown in FIG. 10, a double balloon catheter 120 may optionally be used to unload the heart tissue. Double balloon catheter 120 can provide inflow occlusion to decompress the ventricles, thereby reducing the systolic pressure. This may aid in reducing the ventricular volume and/or in the exclusion of dysfunctional cardiac tissue. Double balloon catheter 120 may optionally be placed using open chest surgery. Alternatively, double balloon catheter 120 may be positioned using minimal invasive techniques, such as via a femoral or subclavian vessels or veins, and optionally being positioned percutaneously.

In some embodiments, double balloon catheter 120 may be positioned so that one balloon is in the superior vena cava and one balloon is in the inferior vena cava, thus blocking most or even essentially all blood flow from the body back to the heart. It may be easier to insert the balloon catheter either into the jugular vein or the femoral vein than it is to place using a cardiac insertion site. An alternative (and in at least some cases faster) way of off-loading the left heart is to inflate a suitably large compliant balloon in the pulmonary artery just above the pulmonic valve (proximal to the branching into the left and right pulmonary arteries). A partially inflated balloon will tend to float into the pulmonary artery from the right atrium, since blood flow carries it into that position. Hence, this may provide another method of decreasing preload on the ventricle.

Figure 11A:
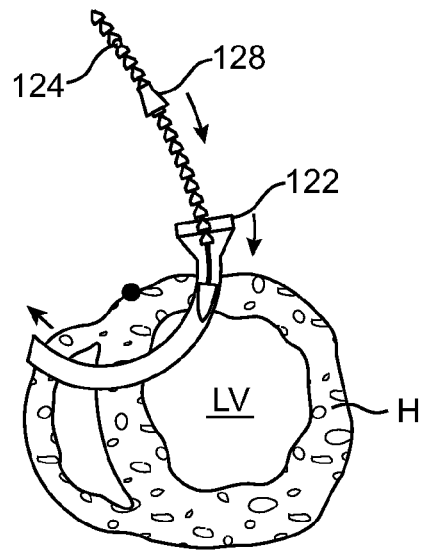
FIGS. 11A-11C schematically illustrate one variation of a transventricular implant and anchor system from a left ventricular approach.
Figure 11B:
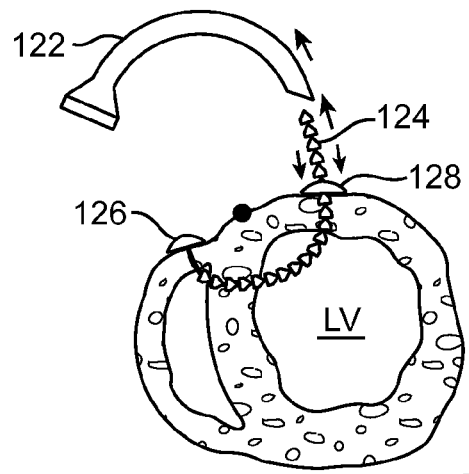
Figure 11C:
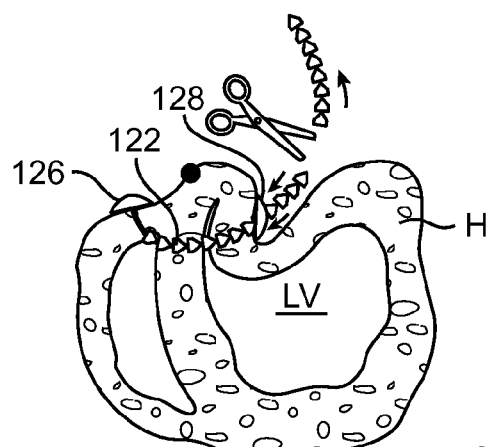

With reference to FIGS. 11A-11C, one variation of a transventricular implant and anchor system deployment from a left ventricular LV approach. A sharpened, curved tissue piercing tubular body 122 pierces the left ventricular wall, the septum, and extends back out through the right ventricular wall. This allows a ratcheted tension member 124 to be introduced through the tissues of the heart within a lumen of tubular body 122, with a first anchor 126 being attached to the tension member after insertion through the tubular body and expanded as described above or affixed after the distal end of the tension member extends free of the heart tissue. Regardless, once the tension member extends into and/or through both ventricles, the tubular body 122 can be withdrawn proximally and a second anchor 128 can be moved distally along the tension member to engage the myocardial surface of the heart, as seen in FIG. 11B. Second anchor 128 may optionally pass through the lumen of tubular body 122 and expand radially, or may be coupled to tension member 124 after the tubular body is withdrawn.

An exemplary ratcheting interface between tension member 124 and second anchor 128 may make use of a series of radial protrusions and/or detents disposed along an axis of the tension member. For example, the tension member may have slide surfaces which taper radially outwardly distally along the tension member to allow the anchor interface to slide sequentially over the slide surfaces in a distal direction, and detent surfaces which are oriented distally to engage corresponding proximally oriented surfaces of the anchor interface so as to inhibit proximal movement of the anchor relative to the tension member. Second anchor 128 may have a ratchet interface structure including (or derived from) the sealing components of a Touhy-Borst valve structure. Such an interface may resiliently deflect to pass the slide surfaces of the tension member and may grab or engage the detent surface when the tension member is pulled distally. Such a valve structure may also be increased in diameter to release the tension member if desired and/or tightened towards its smallest diameter to immovably (and optionally permanently) affix the anchor relative to the tension member. Exemplary embodiments of ratcheting tension member 122 may comprise polymers or metals, optionally comprising a polyester such as Mylar®, a thermoplastic such as Nylon™, a stainless steel, a shape memory allow such as Nitinol™, or the like.

As shown in FIG. 11C, second anchor 128 can be positioned along tension member 122 so as to effectively exclude scar tissue from the left ventricle and/or reduce a volume of the left ventricle. Some portion of tension member 122 may be disposed within the right ventricle, right ventricle scar tissue may be excluded, and/or the volume of the right ventricle may also be reduced. The tension member may be severed using a blade or the like as shown schematically, though some of the tension member may extend into the extracardiac space. In alternative embodiments using different surgical approaches (such as when using the catheter-based systems described above), at least a portion of the tension member may extend into the right ventricle or the like.

Figure 12A:
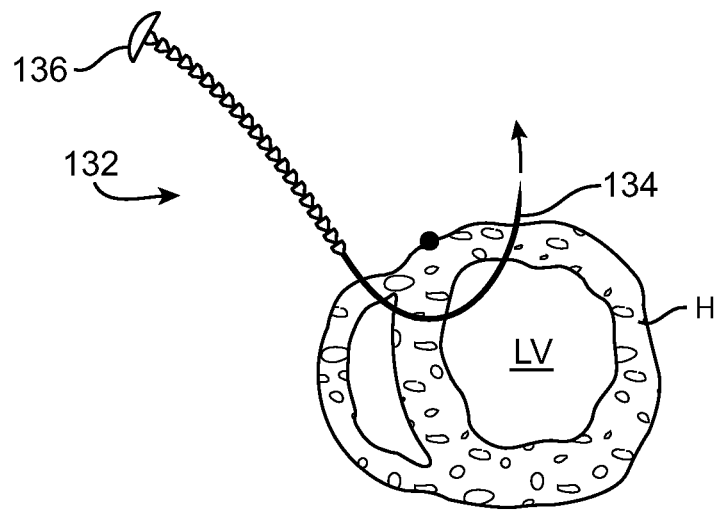
FIGS. 12A and 12B schematically illustrate another variation of a transventricular implant and anchor system from a right ventricular approach.
Figure 12B:
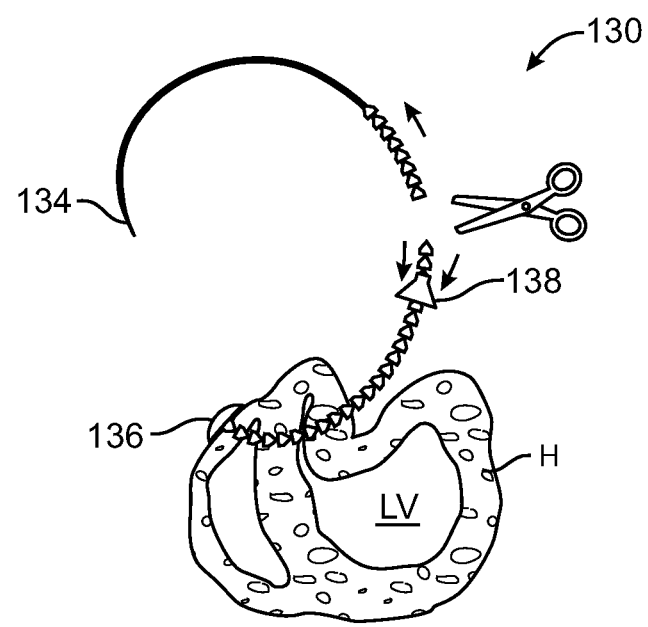

Referring now to FIGS. 12A and 12B, another alternative embodiment of an implant 130 and deployment system makes use of a transventricular approach from the right ventricle. A curved tension member 132 having a distal tissue penetrating end 134 and a proximal anchor 136 affixed thereto is introduced through the wall of the right ventricle, through the septum, across the left ventricle LV, and out through the left ventricular wall. The tension member 132 and affixed anchor 136 are advanced distally so that the anchor engages the surface of the heart, and a second anchor 138 is attached by passing distal end 134 through the anchor. Second anchor 138 is ratcheted proximally along tension member 132 to exclude scar tissue and limit a size of the left ventricle, with the distal end and at least a portion of the tension member that is distal of the positioned anchor being severed and removed from the deployed implant.

Figure 13:
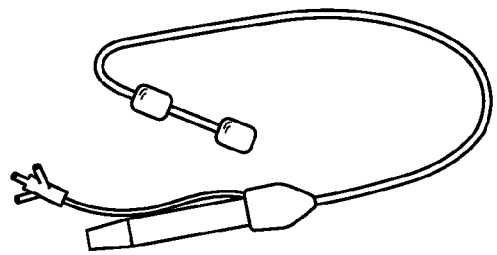
FIG. 13 illustrates a double balloon catheter for unloading of the heart in the method of FIG. 10.
Figure 14A:
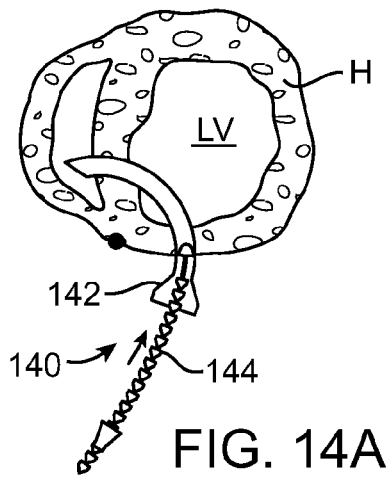
FIGS. 14A-14C schematically illustrate another variation of a transventricular implant and anchor system from a left ventricular approach.
Figure 14B:
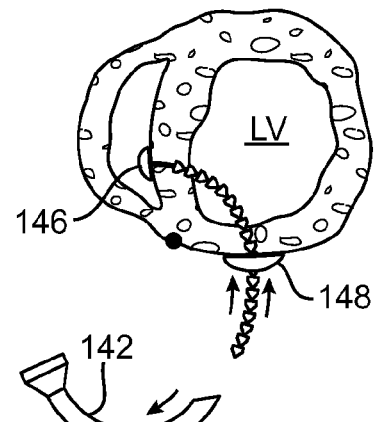
Figure 14C:
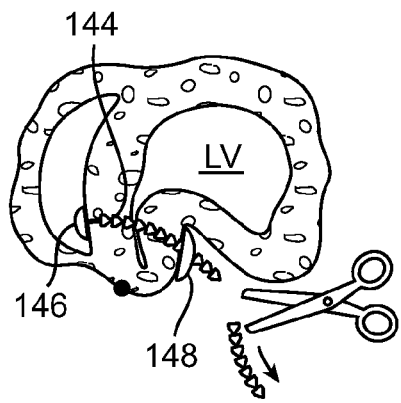

FIG. 13 shows an exemplary double balloon catheter for use as described above with reference to FIGS. 9 and 10. Suitable structures to temporarily inhibit pressure within the heart may be introduced through intravascular or extravascular access. In general, these structures can have the effect, when deployed, of temporarily and reversibly diminishing the left ventricular pressure and output. Suitable pressure inhibiting structures may include occlusive balloons that can be inflated in the right ventricular outflow tract (RVOT) to inhibit left atrial filling. Other suitable occlusive structures may include clamps or the like which may be deployed on an outer surface of the RVOT. Regardless, such devices may be deployed in conjunction with the approximation of the walls to minimize resistance caused by cardiac filling and contraction against normal after load. FIGS. 14A-14C schematically illustrate another transventricular anchor system and deployment from a surgical site outside the heart similar to that of FIGS. 11A-11C, using a tubular body 142 to position a tension member 142 to which first and/or second anchors 146, 148 are ratchetably affixed.

It should be noted that the systems and methods described herein for excluding scar tissue and reducing a size of a chamber of the heart may make use of a plurality of different implants of different types and even different surgical approaches. For example, while systems may include a plurality of implants deployed from a site outside the heart (such as the embodiments shown in FIGS. 11A-11C, 12A and B, and 14A-14C), alternative systems may include one or more implants of one or more types deployed from outside the heart, along with one or more implants of one or more types deployed from inside the heart using a blood-vessel approach. Systems with a plurality of implants deployed from outside and/or inside the heart may benefit from any of a variety of imaging techniques so that the implant systems effectively exclude scar tissue and limit a size of one or more heart chamber.

Referring now to FIGS. 15A-15E, another related embodiment of a deployment system 150 and implant 152 can be understood, along with a method for its deployment. Anchors 154, 156 and tension member 158 are preloaded into an outer sheath 160 of delivery system 150. Outer sheath 160 has a proximal end (not shown) and a distal end 162, with the distal end being configured for penetrating through tissues bordering a chamber of a heart, such as the left ventricular wall W and septum S. Along with or instead of a sharpened distal tip, distal end 162 of sheath 160 may employ an energy delivery structure such as an electrosurgical cautery surface, a powered mechanical structure such as an automated punch or rotary cutter, an optical energy delivery structure such as a laser refracting surface, or the like. Distal end 162 will also open to allow passage of anchors 154, 156, with the tip optionally being passively deflected by the anchors, steerable or articulating to allow passage of the anchors, or the like. Distal tip 162 preferably has a curved shape with sufficient rigidity to distally penetrate tissues and allow adequate motion for deployment of the anchors.

Figure 15A:
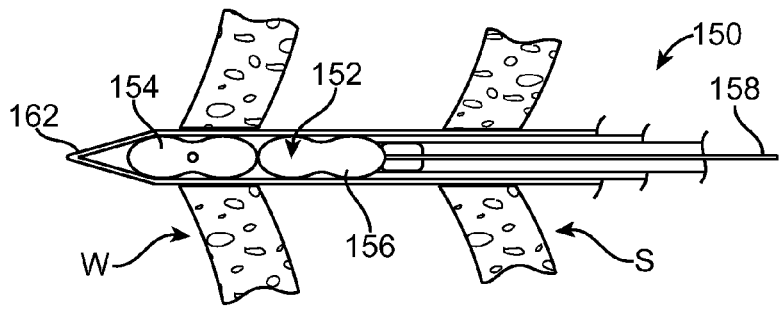
FIGS. 15A-15E are cross sections schematically illustrating deployment of an alternative implant structure so as to approximate the tissues of a heart, with the implant here employing anchors that rotate to a large-profiled deployed configuration relative to the tension member.
Figure 15B:
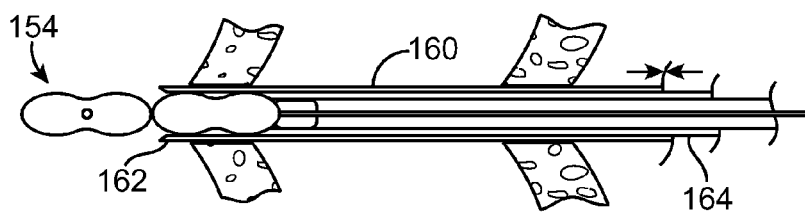

As illustrated in FIG. 15A, delivery system 150 may optionally puncture the septum S, travel across the left ventricle to the free wall W and puncture the free wall. A distal anchor 154 can then be deployed as illustrated in FIG. 15B by retracting outer sheath 160 proximally, and/or by distally advancing an inner sheath 164 or other body disposed within the outer sheath, either of which can act to push open the distal tip 162 and expel the distal anchor 154 from the delivery system 150. As tension member 158 is affixed to distal anchor 154 (see FIG. 15C), the components of delivery system 150 can be retracted proximally from the free wall W leaving the distal anchor 154 to engage and anchor against the distal surface of the left ventricular wall.

Figure 15C:
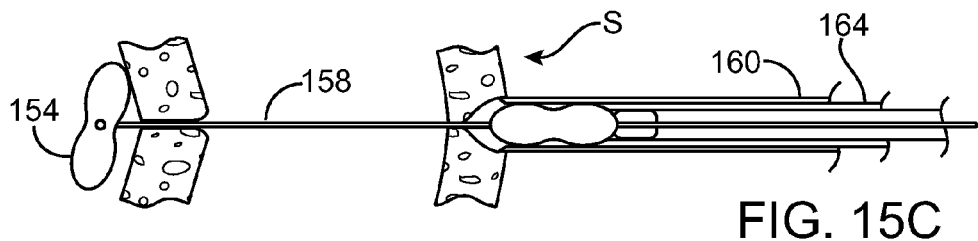
Figure 15D:
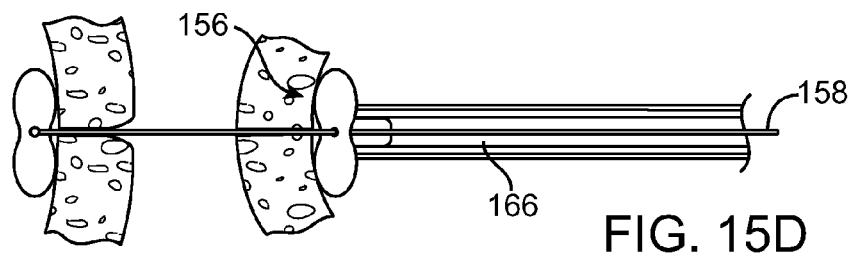
Figure 15E:
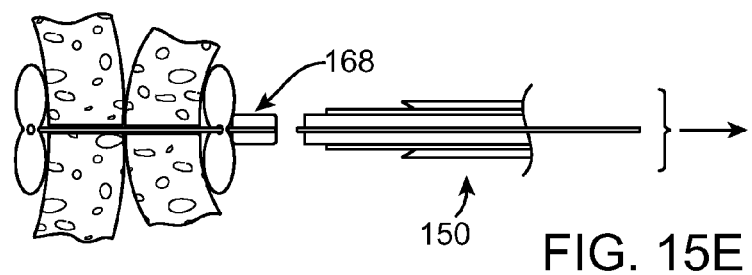

As described above, the distal anchor may optionally expand laterally by articulation of arms or the like. Alternatively, as seen in FIGS. 15A-C, the anchor may increase in its lateral profile by rotation of an elongate structure from a narrow profile orientation to a larger profile orientation. Regardless, outer sheath 160 and other components of the delivery system 150 may be retracted proximally from the left ventricular free wall W and proximal anchor 156 can be deployed so as to engage the septum S as can be understood with reference to FIGS. 15C and 15D.

Once the anchors are positioned, tension may be applied between the members by pulling proximally on a proximal extension of tension member 158, and/or by pushing distally against an anchor stop 168 using an inner tubular body 166 of deployment system 150. Anchor stop 168 may comprise a one-way ratchet mechanism, a latchable or lockable structure configured for being affixed to tension member 158, or the like. Tension member 158 may be trimmed flush to the anchor and/or anchor stop once the left ventricular wall W and septum S have been brought together with the desired tension.

Optionally, the tension force applied to tension member 158 may be predetermined or preset using a spring or other biasing structure, weights, or the like. The tensioning force may be selected to be greater than the tension experienced by the tension member 158 during systole, but less than the tension applied by the heart structures during diastole. As a result, the tension member 158 would move the anchors 154, 156 towards each other selectively between pressure peaks in the left ventricle. This will result in incremental ratcheting of the anchor locations into engagement, avoiding excessive forces being applied against the heart tissue. In other embodiments, surgical personnel may manually or otherwise apply gradually increasing forces until the tissues begin to move towards each other, approximation forces may be enhanced during systole (manually or automatically) in response to an output signal from a blood pressure sensor, or a mechanism may inhibit the application of tension forces in response to blood pressure peaks or the like. Some further alternatives can be employed to selectively approximate the tissues while pressures in the heart chamber are temporarily reduced, including rapid pacing of the heart, occluding blood flow into the heart or heart chamber, and the like.

Optionally, distal end 162 of sheath 160 or some other distal structure of delivery system 150 may be configured to orient one or both of anchors 154, 156 as they are deployed. The anchors may have through holes that are positioned or oriented to preferentially orient the anchors in a desired alignment. Anchor geometry may be determined to distribute contact forces between the anchor and the tissue in a desirable distribution. If tension member 158 is not tensioned sufficiently to give tissue-to-tissue contact and/or sealing, and/or if it is otherwise desirable, the anchor may include a sealing member to inhibit blood or other fluid leakage from the heart chamber.

Figure 16:
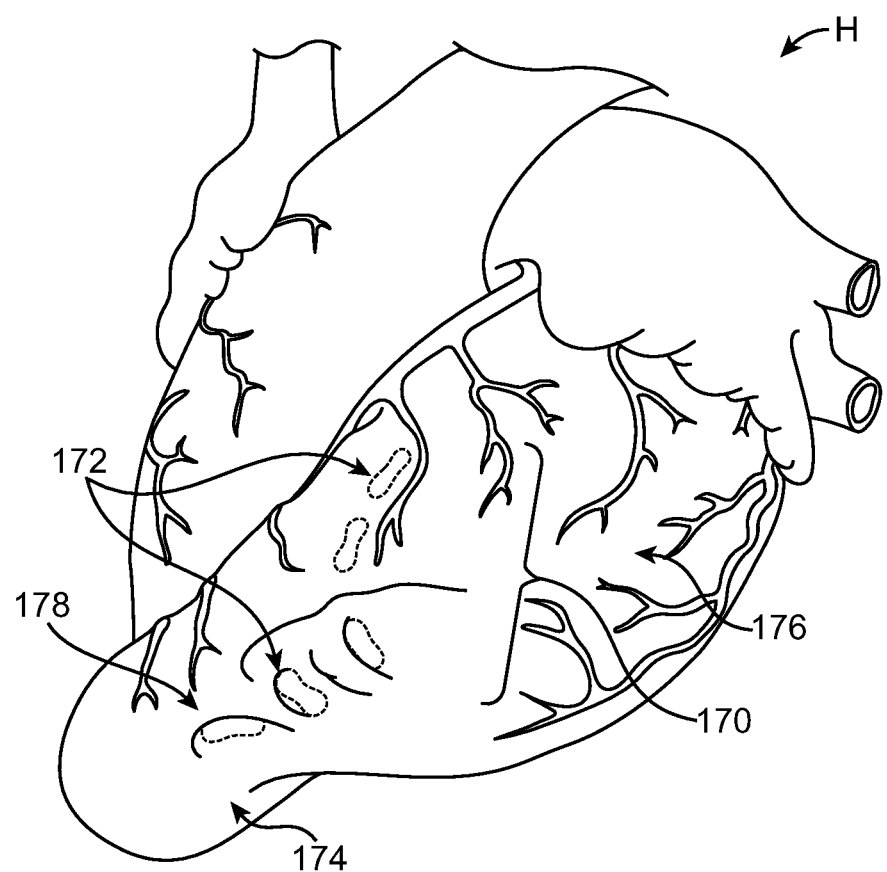
FIG. 16 illustrates an outer surface of a heart in which a pattern of implants has been deployed to effectively exclude scar tissue and provide a desired volumetric reshaping of the chamber of the heart.

Referring now to FIG. 16, treatments will often employ a pattern 170 of anchors 172 (and their associated implants) to effectively exclude at least a portion of infarcted tissue 174 from a remaining heart chamber 176. The pattern 170 will effect an overall volumetric remodeling or reshaping of chamber 176 of heart H, typically by excluding a distended volume and/or circumference 178, with the excluded region of the heart often having expanded gradually over time due to disease progression of congestive heart failure.

The amount of infarcted tissue to be excluded may be determined using techniques similar to those that have been developed for more conventional congestive heart failure surgical therapies. For example, the determination of the desired remaining heart chamber volume and shape may employ aspects of that method used in determining the size of the Blue Egg™ heart treatment sizing tool, which is commercially available from Estech of San Ramon, Calif.

Figures 19A, 19B:
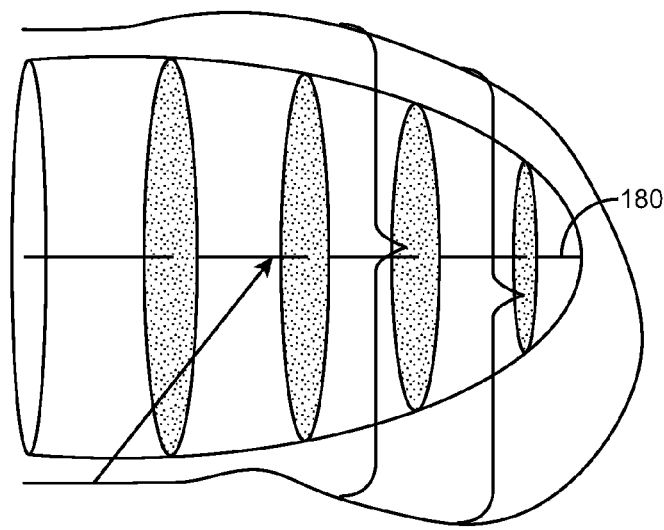
FIGS. 19A and 19B schematically illustrate the processor system and method for determining an appropriate pattern of implant anchor locations so as to volumetrically reshape the chamber of the heart.

Calculation of a desired change in volumetric shape of a heart chamber can be understood with reference to FIGS. 19A and 19B. Circumference reductions in centimeters may be calculated at each of a plurality of discrete cross sections of the heart based on a number of factors, including the body surface area (BSA), the desired left ventricular end-diastolic volume (LVEDV), the location of the cross section along the long axis 180, the measured and desired end diastolic diameter, and the like. Note that the overall desired volumetric shape of the treated heart may be provided by calculating an appropriate change to one or more of the heart chamber cross sections, and by determining appropriate sizes for the other cross sections from the location along the long axis 180. The treated size of the previously calculated cross sections may also be used.

In an exemplary embodiment, the desired volumetric shape and/or pre-treatment volumetric shape may be based on a geometrical model of a portion of the heart. More specifically, the targeted ventricular shape of the reconstructed volume is based on a model of a portion of the left ventricle (LV). That portion is modeled as a truncated prolate spheroid with the long axis extending from the mitral valve to the LV apex and the short axis measured perpendicular to that axis, also sometimes referred to as the LV diameter. The truncated cap corresponds to 45% of the volume of the non-truncated version. The long axis of the truncated model is 60% as long as the long axis of the non-truncated prolate spheroid. The maximum diameter is assumed to be 80% of the long axis (full distance from mitral valve to LV apex). The "original" shape of the prolate spheroid is quite elongated; the short axis is only 48% as long as the long axis. This model of the target LV shape is used to determine anchor positions, as described herein. The modeled LV portion may comprise that which extends from adjacent the mitral valve to the apex, so that (for example) the outflow track of the left ventricle may not be included in the model.

In general, the reduction of diameter and volume may be inferior to the base of the papillary muscles so as to avoid interfering with the function of the papillary muscles or chordae. The short axis measurement to the apex may also be restored via this approach. Anchor locations and implant deployment may be patterned so that the distance between anchor pairs of an implant is equivalent to the desired circumference reduction for a given cross section. Suitable size reduction calculations and approaches will often be based on patient body surface area, and will often take into account the diameter of the left ventricle prior to treatment for each distance from the mitral annulus. The location and size of scar to be excluded will also be identified and considered. A desired volumetric shape for the treated chamber of the heart can be defined by a desired diameter at each cross section along the longitudinal axis so as to promote good heart function for the remaining contractile myocardium. These size reduction considerations can be used to generate appropriate radius reduction targets, and can also be used to identify an appropriate reduction in the effective length of the left ventricle or other heart chamber. Suitable final target shapes will maintain the appropriate proportions between the volume and radius, thereby creating proper wall tension without overstressing the diseased or healthy tissue. Exemplary overall shapes may include circular cross sections with a longitudinal cross section that is substantially elliptical or parabolic, as illustrated in FIG. 19B.

Figure 17B:
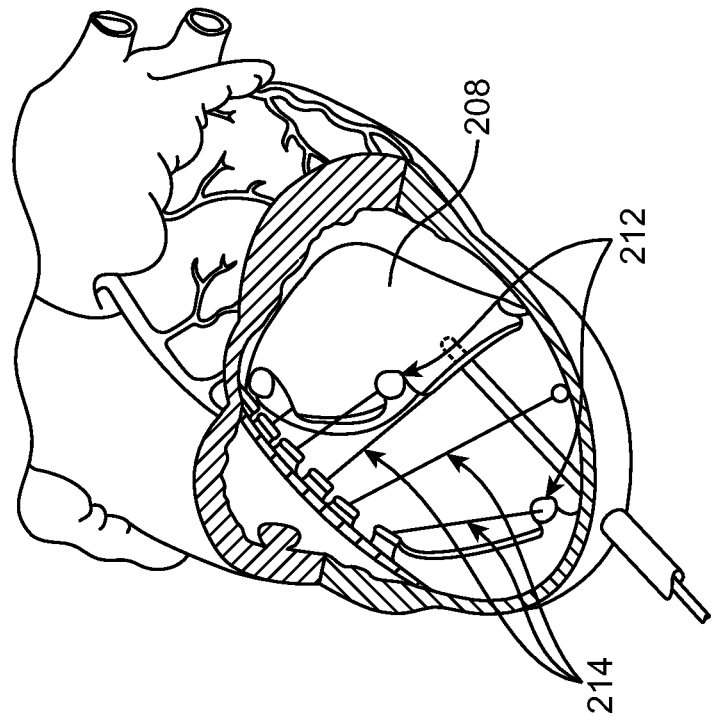
FIGS. 17A and 17B are partial cross sectional views schematically illustrating a partially and fully expanded anchor pattern template for identifying locations of anchors so as to achieve a desired volumetric remodeling of a chamber of the heart.
Figure 17A:
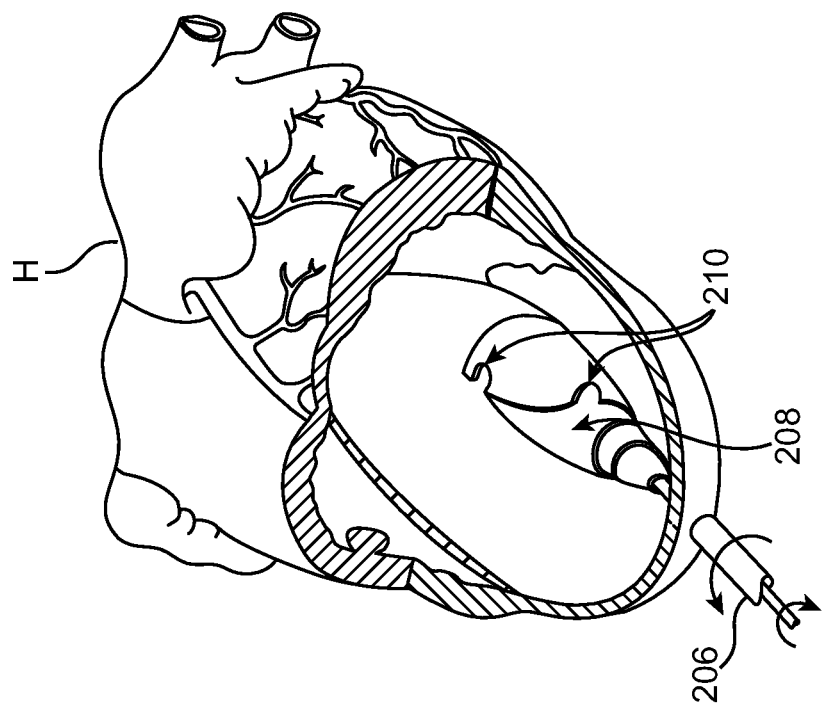
Figure 18A:
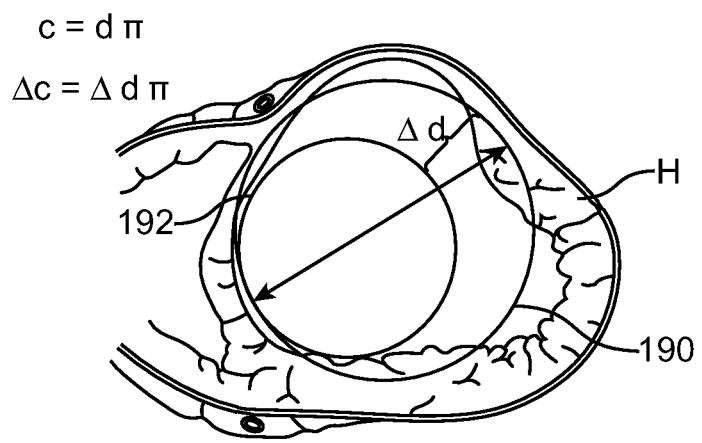
FIGS. 18A-18C schematically illustrate calculations of a desired resizing for one cross section of the heart, and the use of a curved measurement and/or tensile member shortening body for providing a known circumferential reduction (and hence change in diameter) of the heart chamber cross section.
Figure 18B:
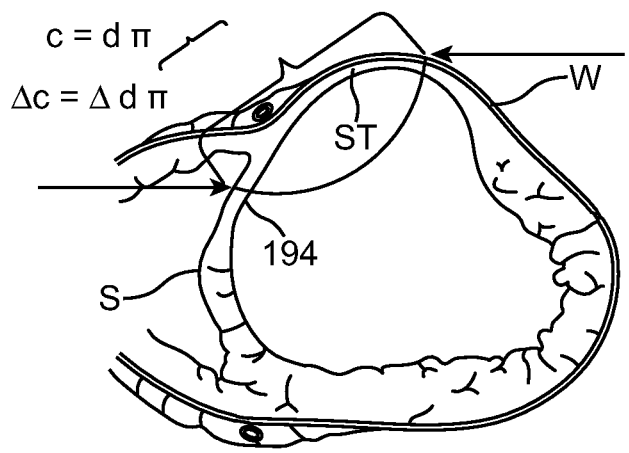
Figure 18C:
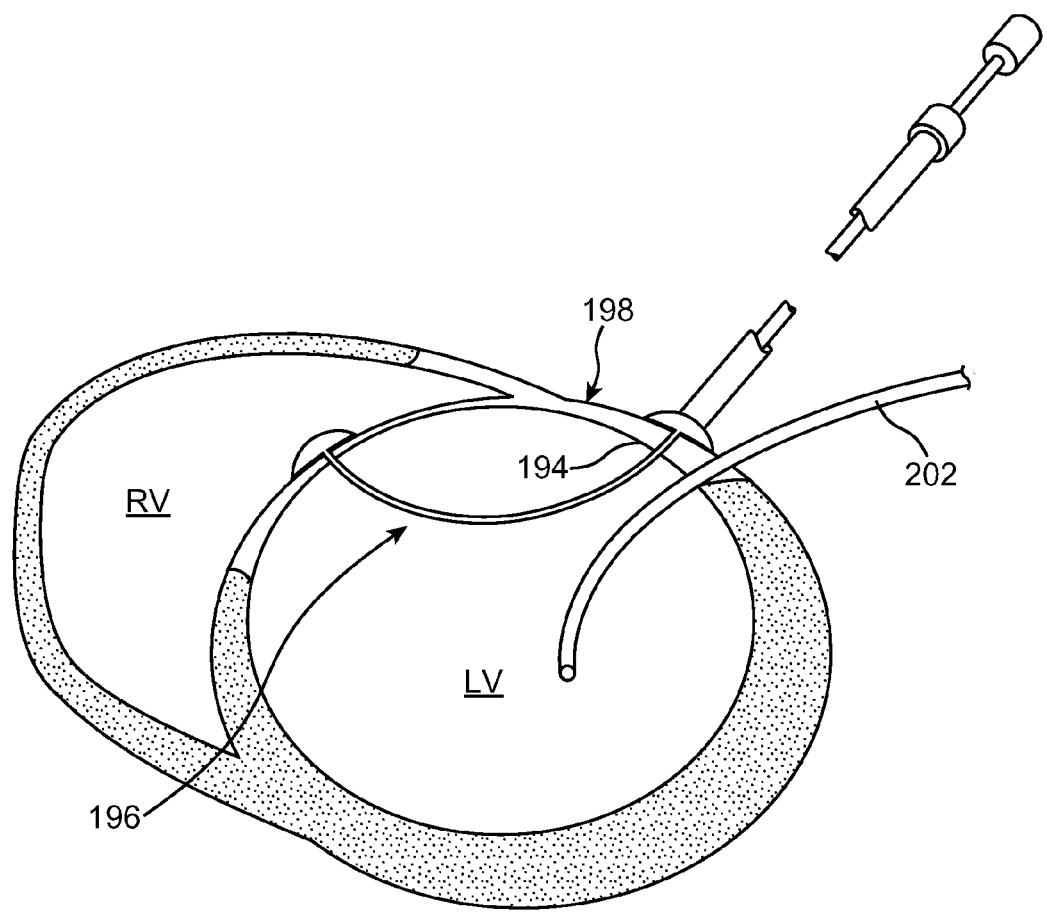

Identifying appropriate anchor locations may be facilitated using a template as illustrated in FIGS. 17A and 17B, and/or using a distance measurement between candidate anchor points as schematically illustrated in FIGS. 18A-C. Details on the calculations of circumferential reduction, as well as the use of curved bodies for identifying appropriate anchor locations, can be understood with reference to FIGS. 18A and 18B. First addressing the calculations graphically represented in these figures, a comparison of the pre-treatment effective diameter 190 of a chamber of heart H at a given axial cross section to a desired diameter 192 (so as to provide a desired volumetric shape to this chamber, for example) identifies a desired change in cross section Δd. The total linear length of circumferential tissue ΔC to be excluded from the chamber at the cross section can then be calculated from $$\Delta C = \Delta d \times \pi$$

FIGS. 18B and 18C schematically illustrate the use of a curving elongate body within the heart to visualize a separation distance between anchor points that will generate the desired reduction in diameter at a given cross section. An initial puncture may be made in either the septum S or free wall W near an edge of scar tissue ST. From initial puncture location 194, a length of steerable or otherwise bent catheter 196 may be fed into the heart chamber, with the length of the catheter body inside the chamber being equivalent to the amount of circumference that is to be removed from that cross section. By bending the catheter body within the left ventricle so that it has a curvature that is substantially equivalent to the curvature of the chamber wall, the catheter can be engaged against a measurably suitable target location for the other anchor. In other words, the length of catheter body 196 within the chamber will be a mirror image of the length of chamber wall 198 between anchor locations, allowing the change in circumference (and thus diameter) to be known.

The length of body within the chamber may be identified using measurement indicia at the distal or proximal ends of catheter body 196, with distal indicia typically being radiopaque, echogenic, or otherwise highly visible under remote imaging. Proximal measurement indicia may be read from the proximal end of the catheter body using an appropriate length element of the delivery system, as can be understood with reference to FIG. 18C. Similar measurements and selected circumference length reductions at each of a plurality of other cross sections of the chamber will generate the desired volumetric shape for effective pumping by the heart.

As noted above, a variety of alternative structures and methods may be used to temporarily reduce pressure within the heart so as to allow volume reduction without imposing excessive trauma on the heart tissues. Along with occlusion of blood flow using a balloon catheter (as illustrated in FIGS. 10 and 13), the ventricle may be paced using a pacing catheter 202 or the like at a rapid rate, so that the ventricle does not effectively pressurize the blood (and hence impose tension on the left ventricular tissues). Other templates may expand using a stent-like structure or the like.

An additional structure and method for identifying appropriate anchor location for deploying one or more implants for excluding scar tissue and/or reshaping a chamber of the heart can be understood with reference to FIGS. 17A and 17B. In this embodiment, a template catheter 206 supports a template 208 that is expandable in vivo. Template 208 is introduced into a chamber of heart H, either through the septum, the apex, or mitral valve. Once template 206 is within the left ventricle, the template can be expanded against the surface of the ventricle in alignment with the infarcted scar tissue. In the embodiment illustrated here, template 208 is radially expanded by unrolling the template from around the axis of the catheter body, with the template material engaging the contractile heart tissue that is to remain bordering the chamber after treatment.

Template 208 includes indicia or targets that are visible under the desired imaging modality to be used during treatment. For example, the targets may be radiopaque, echogenic, easily visible under direct imaging, or the like. Suitable targets may comprise contrast filled bladders, discrete radiopaque markers, or the like. The surgeon may then direct the anchor delivery device through the septum as described above, using the targets to determine an appropriate anchor placement for the distal anchor. Once anchors 212 are positioned and tension members 214 are ready to reduce the chamber volume, template 208 can again be rolled up to a small profile configuration and removed from the chamber.

Once all anchors are placed, the tension members may be tensioned to bring the epicardial tissues together. Some or all of the tension members may be tensioned simultaneously. In some embodiments, some or all of the tension members may be tensioned sequentially. In the event that one or more anchor placement is determined to be inappropriate, the tension member may be cut at the septal wall of the right ventricle, on the outside of the free wall of the left ventricle, or the like.

While exemplary embodiments have been described in some detail for clarity of understanding and by way of example, a variety of modifications, adaptations, and changes will be obvious to those of skill in the art. Hence, the scope of the invention is limited solely by the appended claims.

What is claimed is:

1. A method for treating a diseased heart, the method comprising:
   reducing, in a first cross-section, a first size of a chamber of a heart by decreasing a distance between a first anchor location and a second anchor location, the anchor locations disposed near edges of a diseased tissue bordering the chamber;
   determining, for a second cross-section, a second reduction in size of the chamber, the second reduction in size being determined in response to:
      an offset between the first cross-section and the second cross-section, and
      a magnitude of the first reduction in cross-section of the chamber identified from a length of a catheter body extending between the first anchor location and the second anchor location; and
   effecting the determined second reduction in size of the chamber by deploying third and fourth anchors into tissues of the heart bordering the chamber, and by reducing a length of a tension member under bias by a fixed preset force extending between the third and fourth anchors only while pressure within the chamber is less than systolic;
   wherein the chamber in the first cross section has a first cross-section diameter defining a first curvature, wherein the catheter body has an axis between the first anchor and the second anchor, the axis having an axis curvature substantially corresponding to the first curvature, the magnitude of the first reduction in cross-section determined by measuring a length of the axis between the first anchor location and the second anchor location, and wherein decreasing the distance between the first anchor location and the second anchor location effects a change from the first cross-section diameter to a first reduced diameter.

2. The method of claim 1, wherein a magnitude of the second reduction in cross-section is identified from a length of a body extending between locations of the third anchor and the fourth anchor.

3. The method of claim 2, wherein the chamber in the second cross section has a second cross-section diameter defining a second curvature, wherein the body has a particular axis between the third anchor and the fourth anchor, the particular axis having an axis curvature substantially corresponding to the second curvature, the magnitude of the second reduction in cross-section determined by a length of the particular axis between the third anchor location and the fourth anchor location.

4. The method of claim 1, further comprising determining the second reduction in size in response to a diseased size of the chamber in the second cross section before the second reduction.

5. The method of claim 4, wherein the second reduction in size is determined by computing a change in length of a circumference of the second cross section from a desired change in diameter of the second cross section.

6. The method of claim 1, further comprising determining, for each of a plurality of cross-sections, an associated desired reduction in size of the chamber, the associated reduction in size being determined in response to:
   a diseased size of the chamber in the cross-section before the associated reduction,
   an offset between the first cross-section and the cross-section, and
   a magnitude of the first reduction,
   so as to define a desired volumetric shape of the chamber; and
   effecting each determined reduction in size of the chamber by deploying associated anchors into tissues of the heart bordering the chamber, and by reducing a length of a tension member extending between the anchors to generate the desired volumetric shape of the chamber.

7. A method for treating a diseased heart, the method comprising:
   deploying an anchor pattern template membrane against endocardial surfaces within a chamber of the heart by unrolling the anchor pattern template membrane from a deployment member, the anchor pattern template membrane identifying a plurality of anchor locations;
   deploying a plurality of anchors into tissue of the heart per the aligned template membrane;
   applying, between associated anchors of the plurality of anchors, tension so as to apply force to tissue adjacent the associated anchors and reduce an effective size of the chamber; and
   removing the anchor pattern template membrane from the endocardial surfaces by rolling the anchor pattern template membrane to the deployment member.

8. The method of claim 7, further comprising inserting the anchor pattern template membrane into the chamber in a small-profile configuration and expanding the anchor pattern template membrane to a large-profile configuration within the chamber.

9. The method of claim 7, wherein the anchor pattern template membrane is aligned with scar tissue of the heart, and wherein the desired volumetric shape excludes the scar tissue from the chamber.

* * * * *